United States Patent
Li

(10) Patent No.: US 11,642,397 B2
(45) Date of Patent: May 9, 2023

(54) METHOD AND DRUG FOR PREVENTING OR TREATING OSTEOARTHRITIS

(71) Applicant: TALENGEN INTERNATIONAL LIMITED, Hong Kong (CN)

(72) Inventor: Jinan Li, Shenzhen (CN)

(73) Assignee: TALENGEN INTERNATIONAL LIMITED, Hong Kong (CN)

( * ) Notice: Subject to any disclaimer, the term of this patent is extended or adjusted under 35 U.S.C. 154(b) by 177 days.

(21) Appl. No.: 16/954,159

(22) PCT Filed: Dec. 17, 2018

(86) PCT No.: PCT/CN2018/121535
§ 371 (c)(1),
(2) Date: Jun. 15, 2020

(87) PCT Pub. No.: WO2019/114839
PCT Pub. Date: Jun. 20, 2019

(65) Prior Publication Data
US 2021/0154275 A1    May 27, 2021

(30) Foreign Application Priority Data

Dec. 15, 2017 (WO) ............... PCT/CN2017/116636

(51) Int. Cl.
*A61K 38/48*    (2006.01)
*A61P 19/02*    (2006.01)

(52) U.S. Cl.
CPC ............ *A61K 38/484* (2013.01); *A61P 19/02* (2018.01); *C12Y 304/21007* (2013.01)

(58) Field of Classification Search
CPC .......... A61K 38/484; C12Y 304/21007; A61P 19/02
See application file for complete search history.

(56) References Cited

U.S. PATENT DOCUMENTS

| 6,475,784 | B1 | 11/2002 | Papkoff |
| 2019/0365871 | A1 | 12/2019 | Li |

FOREIGN PATENT DOCUMENTS

| CN | 105664145 A | 6/2016 |
| EP | 3556381 A1 | 10/2019 |
| EP | 3725326 A1 | 10/2020 |
| JP | 2002520367 A | 7/2002 |
| TW | 201828976 A | 8/2018 |
| WO | 199965519 A1 | 12/1999 |
| WO | 200003726 A1 | 1/2000 |
| WO | 2018108165 A1 | 6/2018 |
| WO | 2019114839 A1 | 6/2019 |

OTHER PUBLICATIONS

Extended European Search Report, dated Jan. 27, 2021, for European Patent Application No. 18888391.2, 9 pages.

Sanderson-Smith, M.L. et al. (2012). "Bacterial Plasminogen Receptors: Mediators of a Multifaceted Relationship," Jornal of Biomedicine and Biotechnology 2012(272148):1-14.
Steinmeyer, J. et al. (May 20, 2006, e-pub. Apr. 17, 2006). "Oral Treatment Options For Degenerative Joint Disease—Presence and Future," Advanced Drug Delivery Reviews 58(2):168-211.
Alexander, C.M. et al. (1989). "Proteinases and Extracellular Matrix Remodeling," Curr. Opin. Cell Biol. 1:974-982.
Alexander, C.M. et al. (1991). "Chapter 8—Extracellular Matrix Degradation," in Cell Biology of Extracellular Matrix, Hay ED, 2nd ed. (New York: Plenum Press), pp. 255-302.
Andreasen, P.A. et al. (1997). "The Urokinase-Type Plasminogen Activator System In Cancer Metastasis: A Review," Int. J. Cancer 72:1-22.
Berenbaum, F. (Jan. 2013). "Osteoarthritis as an Inflammatory Disease," Osteoarthritis and Cartilage 21(1):16-21, 1 page.
Collen, D. (2001). "Ham-Wasserman Lecture: Role Of The Plasminogen System In Fibrin-Homeostasis and Tissue Remodeling," Hematology (Am. Soc. Hematol. Educ. Program), pp. 1-9.
Collen, D. et al. (Dec. 15, 1991). "Basic and Clinical Aspects Of Fibrinolysis and Thrombolysis," Blood 78 (12):3114-3124.
Combe, R. et al. "The Monosodium Iodoacetate Model Of Osteoarthritis: A Model Of Chronic Nociceptive Pain In Rats?," Neurosci Lett. 370 (2004) 236-240.
Daci, E. et al. (Jul. 2000). "Bone Resorption Induced by 1α,25 Dihydroxyvitamin D3 In Vivo Is Not Altered by Inactivation of the Plasminogen Activator Inhibitor 1," Bone 27(1):97-102.
Duque, G. et al. (Jul. 2011). "Interferon-γ Plays a Role in Bone Formation In Vivo and Rescues Osteoporosis in Ovariectomized Mice," Journal of Bone and Mineral Research 26(7):1472-1483.
Glyn-Jones, S. et al. (Jul. 2015, e-pub. Mar. 4, 2015). "Osteoarthritis," Lancet. 386(9991):376-387.
Hagan, J.J. et al. (Apr. 1960). "Purification and Biochemical Properties Of Human Plasminogen," J Biol Chem. 235:1005-1010.
Handout on Health (Apr. 2015). "Scleroderma," National Institute of Arthritis and Musculoskeletal and Skin Diseases. 46 pages.
Hardingham, T.E. et al. (2010). "Cartilage, SOX9 and Notch Signals In Chondrogenesis," Journal of Anatomy 209 (4):469-480, 12 pages.
He, C.S. et al. (Apr. 1989). "Tissue Cooperation In a Proteolytic Cascade Activating Human Interstitial Collagenase," Proc. Natl. Acad. Sci. USA 86:2632-2636.
Hunt, J.A. et al. (2008, e-pub. Aug. 14, 2008). "Simplified Recombinant Plasmin: Production and Functional Comparison Of A Novel Thrombolytic Molecule With Plasma-Derived Plasmin [J]," Thromb Haemost 100(3):413-419.
International Preliminary Report on Patentability, dated Jun. 16, 2020, for PCT Application No. PCT/CN2018/121535, filed Dec. 17, 2018, 6 pages.

(Continued)

*Primary Examiner* — Ruth A Davis
(74) *Attorney, Agent, or Firm* — Morrison & Foerster LLP

(57) ABSTRACT

The present invention relates to a method and a drug for preventing or treating osteoarthritis by plasminogen. Specifically, the present invention involves administering an effective amount of plasminogen to an osteoarthritis subject for treating the osteoarthritis. In addition, the present invention further relates to an osteoarthritis treatment drug comprising plasminogen, a product, and a kit.

15 Claims, 7 Drawing Sheets

Specification includes a Sequence Listing.

(56) References Cited

OTHER PUBLICATIONS

International Search Report, dated Mar. 21, 2019, for PCT Application No. PCT/CN2018/121535, filed Dec. 17, 2018, 5 pages.
Kamekura, S. et al. (Jul. 2005). "Osteoarthritis Development In Novel Experimental Mouse Models Induced By Knee Joint Instability," Osteoarthritis and Cartilage 13(7):632-641.
Li, G. et al. (2013). "Subchondral Bone In Osteoarthritis: Insight Into Risk Factors and Microstructural Changes," Arthritis Research & Therapy 15:223, 12 pages.
MacKay, A.M. et al. (1998). "Chondrogenic Differentiation Of Cultured Human Mesenchymal Stem Cells From Marrow," Tissue Engineer. 4(4):415-428.
Marder V.J. et al. (2010). "Direct Fibrinolytic Agents: Biochemical Attributes, Preclinical Foundation and Clinical Potential," J Journal of Thrombosis and Haemostasis 8(3):433-444.
Medynski, D. et al. (2007, e-pub. Oct. 26, 2006). "Refolding, Purification, and Activation Of Miniplasminogen and Microplasminogen Isolated From E. coli Inclusion Bodies," J. Protein Expression & Purification 52(2):395-402.
Mignatti, P. et al. (Jan. 1993). "Biology and Biochemistry Of Proteinases In Tumor Invasion," Physiol Rev. 73 (1):161-195.
Nagai, N. et al. (2003). "Recombinant Human Microplasmin: Production and Potential Therapeutic Properties," Journal of Thrombosis and Haemostasis 1(2):307-313.
Ogbonna, A.C. et al. (Apr. 2013). "Pain-Like Behaviour and Spinal Changes In The Monosodium Iodoacetate Model Of Osteoarthritis In C57Bl/6 Mice," Eur J Pain 17(4):514-526.
Ostergaard, K. et al. (Apr. 1999). "Validity Of Histopathological Grading Of Articular Cartilage From Osteoarthritic Knee Joints," Ann Rheum Dis. 58(4):208-213.
Raum, D. et al. (May 30, 1980). "Synthesis Of Human Plasminogen By The Liver," Science 208:1036-1037.
Razzaque, M.S. et al. (Apr. 2006). "Premature Aging-Like Phenotype In Fibroblast Growth Factor 23 Null Mice Is A Vitamin D-Mediated Process," FASEB J. 20(6):720-722, 15 pages.
Rifkin, D.B. et al. (1990). "Growth Factor Control Of Extracellular Proteolysis," Cell Differ. Dev. 32:313-318.
Rifkin, D.B. et al. (1999). "Proteolytic Control Of Growth Factor Availability," APMIS 107:80-85.
Robbins, K.C. et al. (Jan. 1965). "Further Studies on the Purification and Characterization of Human Plasminogen and Plasmin," Journal of Biological Chemistry 240(1):541-550.
Saksela, O. et al. (1988). "Cell-Associated Plasminogen Activation: Regulation and Physiological Functions," Annu. Rev. Cell Biol. 4:93-126.
Sato, K. et al. (2017, e-pub. Feb. 28, 2017). "Effect of Epigallocatechin-3-Gallate On The Increase In Type II Collagen Accumulation In Cartilage-Like MSC Sheets," Bioscience, Biotechnology, and Biochemistry 81(6):1241-1245.
Sottrup-Jensen, L. et al. (Jul. 1975). "Amino-Acid Sequence Of Activation Cleavage Site In Plasminogen Homology With 'Pro' Part Of Prothrombin," Proc. Natl. Acad. Sci. USA 72(7):2577-2581.
Stoppelli, M.P. et al. (Aug. 1985). "Differentiation-Enhanced Binding Of The Amino-Terminal Fragment Of Human Urokinase Plasminogen Activator To A Specific Receptor On U937 Monocytes," Proc. Natl. Acad. Sci. USA 82:4939-4943.
Summaria, L. et al. (Jun. 25, 1976). "Isolation and Characterization Of The Affinity Chromatography Forms Of Human Glu- and Lys-Plasminogens And Plasmins," J Biol Chem. 251(12):3693-3699.
Van Der Kraan, P.M. et al. (Feb. 1990). "Degenerative Knee Joint Lesions In Mice After A Single Intra-Articular Collagenase Injection. A New Model Of Osteoarthritis," J Exp Pathol (Oxford) 71(1):19-31.
Van Lent, P. et al. (May 2012). "Active Involvement of 'Alarmins' S100A8 and S100A9 in the Regulation of Synovial Activation and Joint Destruction During Mouse and Human Osteoarthritis," Arthritis Rheum. 64(5):1466-1476, 3 pages.
Vassalli, J.D. et al. (Jan. 1985). "A Cellular Binding Site For The Mr 55,000 Form Of The Human Plasminogen Activator, Urokinase," J. Cell Biol. 100:86-92.
Waisman, D.M. (2003). Plasminogen: Structure, Activation, and Regulation, 18 pages.
Weinreb, M. et al. (1990). "Different Pattern Of Alkaline Phosphatase, Osteopontin, and Osteocalcin Expression In Developing Rat Bone Visualized By In Situ Hybridization," J Bone Miner Res 5(8):831-842.
Werb, Z. et al. (May 5, 1977). "Endogenous Activation Of Latent Collagenase By Rheumatoid Synovial Cells. Evidence For a Role Of Plasminogen Activator," N. Engl. J. Med. 296(18):1017-1023.
Wiman, B. et al. (1975). "Structural Relationship Between 'Glutamic Acid' and 'Lysine' Forms Of Human Plasminogen and Their Interaction With The NH2-Terminal Activation Peptide As Studied By Affinity Chromatography," Eur. J. Biochem. 50:489-494.
Written Opinion, dated Mar. 21, 2019, for PCT Application No. PCT/CN2018/121535, filed Dec. 17, 2018, 5 pages (English Translation).
Goldring, M.B. et al. (Sep. 2011). "Inflammation in Osteoarthritis," Curr. Opin. Rheumatol. 23(5):476-478, 13 pages.
Raghu, H. et al. (Jun. 2014). "Plasminogen is a Joint-Specific Positive- or Negative- Determinant of Arthritis Pathogenesis," Arthritis Rheumatol. 66(6):1504-1516, 43 pages.

SEQUENCE LISTING

<160> NUMBER OF SEQ ID NOS: 14

<210> SEQ ID NO 1
<211> LENGTH: 2376
<212> TYPE: DNA
<213> ORGANISM: Artificial sequence
<220> FEATURE:
<223> OTHER INFORMATION: nucleotide sequence coding for the natural plasminogen (Glu-PLG,Glu-plasminogen)without the signal peptide

<400> SEQUENCE: 1

```
gagcctctgg atgactatgt gaatacccag ggggcttcac tgttcagtgt cactaagaag      60
cagctgggag caggaagtat agaagaatgt gcagcaaaat gtgaggagga cgaagaattc     120
acctgcaggg cattccaata tcacagtaaa gagcaacaat gtgtgataat ggctgaaaac     180
aggaagtcct ccataatcat taggatgaga gatgtagttt tatttgaaaa gaaagtgtat     240
ctctcagagt gcaagactgg gaatggaaag aactacagag ggacgatgtc caaaacaaaa     300
aatggcatca cctgtcaaaa atggagttcc acttctcccc acagacctag attctcacct     360
gctacacacc cctcagaggg actggaggag aactactgca ggaatccaga caacgatccg     420
caggggccct ggtgctatac tactgatcca gaaaagagat atgactactg cgacattctt     480
gagtgtgaag aggaatgtat gcattgcagt ggagaaaact atgacggcaa aatttccaag     540
accatgtctg gactggaatg ccaggcctgg gactctcaga gcccacacgc tcatggatac     600
attccttcca aatttccaaa caagaacctg aagaagaatt actgtcgtaa ccccgatagg     660
gagctgcggc cttggtgttt caccaccgac cccaacaagc gctgggaact ttgtgacatc     720
ccccgctgca acacctcc accatcttct ggtcccacct accagtgtct gaagggaaca     780
ggtgaaaact atcgcgggaa tgtggctgtt accgtgtccg ggcacacctg tcagcactgg     840
agtgcacaga cccctcacac acataacagg acaccagaaa acttcccctg caaaaatttg     900
gatgaaaact actgccgcaa tcctgacgga aaagggccc catggtgcca tacaaccaac     960
agccaagtgc ggtgggagta ctgtaagata ccgtcctgtg actcctcccc agtatccacg    1020
gaacaattgg ctcccacagc accacctgag ctaacccctg tggtccagga ctgctaccat    1080
ggtgatggac agagctaccg aggcacatcc tccaccacca ccacaggaaa gaagtgtcag    1140
tcttggtcat ctatgacacc acaccggcac cagaagaccc cagaaaacta cccaaatgct    1200
ggcctgacaa tgaactactg caggaatcca gatgccgata aggccctg gtgtttttacc    1260 acagacccca gcgtcaggtg ggagtactgc aacctgaaaa aatgctcagg aacagaagcg    1320
agtgttgtag cacctccgcc tgttgtcctg cttccagatg tagagactcc ttccgaagaa    1380
gactgtatgt ttgggaatgg gaaaggatac cgaggcaaga gggcgaccac tgttactggg    1440
acgccatgcc aggactgggc tgcccaggag ccccatagac acagcatttt cactccagag    1500
```

```
acaaatccac gggcgggtct ggaaaaaaat tactgccgta accctgatgg tgatgtaggt    1560
ggtccctggt gctacacgac aaatccaaga aaactttacg actactgtga tgtccctcag    1620
tgtgcggccc cttcatttga ttgtgggaag cctcaagtgg agccgaagaa atgtcctgga    1680
agggttgtag ggggtgtgt  ggcccaccca cattcctggc cctggcaagt cagtcttaga    1740
acaaggtttg gaatgcactt ctgtggaggc accttgatat ccccagagtg ggtgttgact    1800
gctgcccact gcttggagaa gtccccaagg ccttcatcct acaaggtcat cctgggtgca    1860
caccaagaag tgaatctcga accgcatgtt caggaaatag aagtgtctag gctgttcttg    1920
gagcccacac gaaagatat  tgccttgcta aagctaagca gtcctgccgt catcactgac    1980
aaagtaatcc cagcttgtct gccatcccca aattatgtgg tcgctgaccg gaccgaatgt    2040
ttcatcactg gctggggaga aacccaaggt acttttggag ctggccttct caaggaagcc    2100
cagctccctg tgattgagaa taaagtgtgc aatcgctatg agtttctgaa tggaagagtc    2160
caatccaccg aactctgtgc tgggcatttg gccggaggca ctgacagttg ccagggtgac    2220
agtggaggtc ctctggtttg cttcgagaag gacaaataca ttttacaagg agtcacttct    2280
tggggtcttg gctgtgcacg ccccaataag cctggtgtct atgttcgtgt ttcaaggttt    2340
gttacttgga ttgagggagt gatgagaaat aattaa                              2376
```

<210> SEQ ID NO 2
<211> LENGTH: 791
<212> TYPE: PRT
<213> ORGANISM: Artificial sequence
<220> FEATURE:
<223> OTHER INFORMATION: amino acid sequence of the natural plasminogen
      (Glu-PLG,Glu-plasminogen) without the signal peptide

<400> SEQUENCE: 2

```
Glu Pro Leu Asp Asp Tyr Val Asn Thr Gln Gly Ala Ser Leu Phe Ser
1               5                   10                  15

Val Thr Lys Lys Gln Leu Gly Ala Gly Ser Ile Glu Glu Cys Ala Ala
            20                  25                  30

Lys Cys Glu Glu Asp Glu Glu Phe Thr Cys Arg Ala Phe Gln Tyr His
        35                  40                  45

Ser Lys Glu Gln Gln Cys Val Ile Met Ala Glu Asn Arg Lys Ser Ser
    50                  55                  60

Ile Ile Ile Arg Met Arg Asp Val Val Leu Phe Glu Lys Lys Val Tyr
65                  70                  75                  80

Leu Ser Glu Cys Lys Thr Gly Asn Gly Lys Asn Tyr Arg Gly Thr Met
                85                  90                  95

Ser Lys Thr Lys Asn Gly Ile Thr Cys Gln Lys Trp Ser Ser Thr Ser
            100                 105                 110

Pro His Arg Pro Arg Phe Ser Pro Ala Thr His Pro Ser Glu Gly Leu
        115                 120                 125

Glu Glu Asn Tyr Cys Arg Asn Pro Asp Asn Asp Pro Gln Gly Pro Trp
    130                 135                 140

Cys Tyr Thr Thr Asp Pro Glu Lys Arg Tyr Asp Tyr Cys Asp Ile Leu
145                 150                 155                 160

Glu Cys Glu Glu Glu Cys Met His Cys Ser Gly Glu Asn Tyr Asp Gly
                165                 170                 175

Lys Ile Ser Lys Thr Met Ser Gly Leu Glu Cys Gln Ala Trp Asp Ser
            180                 185                 190

Gln Ser Pro His Ala His Gly Tyr Ile Pro Ser Lys Phe Pro Asn Lys
        195                 200                 205
```

```
Asn Leu Lys Lys Asn Tyr Cys Arg Asn Pro Asp Arg Glu Leu Arg Pro
    210                 215                 220

Trp Cys Phe Thr Thr Asp Pro Asn Lys Arg Trp Glu Leu Cys Asp Ile
225                 230                 235                 240

Pro Arg Cys Thr Thr Pro Pro Ser Ser Gly Pro Thr Tyr Gln Cys
                245                 250                 255

Leu Lys Gly Thr Gly Glu Asn Tyr Arg Gly Asn Val Ala Val Thr Val
                260                 265                 270

Ser Gly His Thr Cys Gln His Trp Ser Ala Gln Thr Pro His Thr His
                275                 280                 285

Asn Arg Thr Pro Glu Asn Phe Pro Cys Lys Asn Leu Asp Glu Asn Tyr
    290                 295                 300

Cys Arg Asn Pro Asp Gly Lys Arg Ala Pro Trp Cys His Thr Thr Asn
305                 310                 315                 320

Ser Gln Val Arg Trp Glu Tyr Cys Lys Ile Pro Ser Cys Asp Ser Ser
                325                 330                 335

Pro Val Ser Thr Glu Gln Leu Ala Pro Thr Ala Pro Pro Glu Leu Thr
                340                 345                 350

Pro Val Val Gln Asp Cys Tyr His Gly Asp Gly Gln Ser Tyr Arg Gly
                355                 360                 365

Thr Ser Ser Thr Thr Thr Thr Gly Lys Lys Cys Gln Ser Trp Ser Ser
370                 375                 380

Met Thr Pro His Arg His Gln Lys Thr Pro Glu Asn Tyr Pro Asn Ala
385                 390                 395                 400

Gly Leu Thr Met Asn Tyr Cys Arg Asn Pro Asp Ala Asp Lys Gly Pro
                405                 410                 415

Trp Cys Phe Thr Thr Asp Pro Ser Val Arg Trp Glu Tyr Cys Asn Leu
                420                 425                 430

Lys Lys Cys Ser Gly Thr Glu Ala Ser Val Val Ala Pro Pro Pro Val
                435                 440                 445

Val Leu Leu Pro Asp Val Glu Thr Pro Ser Glu Glu Asp Cys Met Phe
    450                 455                 460

Gly Asn Gly Lys Gly Tyr Arg Gly Lys Arg Ala Thr Thr Val Thr Gly
465                 470                 475                 480

Thr Pro Cys Gln Asp Trp Ala Ala Gln Glu Pro His Arg His Ser Ile
                485                 490                 495

Phe Thr Pro Glu Thr Asn Pro Arg Ala Gly Leu Glu Lys Asn Tyr Cys
                500                 505                 510

Arg Asn Pro Asp Gly Asp Val Gly Gly Pro Trp Cys Tyr Thr Thr Asn
                515                 520                 525

Pro Arg Lys Leu Tyr Asp Tyr Cys Asp Val Pro Gln Cys Ala Ala Pro
    530                 535                 540

Ser Phe Asp Cys Gly Lys Pro Gln Val Glu Pro Lys Lys Cys Pro Gly
545                 550                 555                 560

Arg Val Val Gly Gly Cys Val Ala His Pro His Ser Trp Pro Trp Gln
                565                 570                 575

Val Ser Leu Arg Thr Arg Phe Gly Met His Phe Cys Gly Gly Thr Leu
                580                 585                 590

Ile Ser Pro Glu Trp Val Leu Thr Ala Ala His Cys Leu Glu Lys Ser
                595                 600                 605

Pro Arg Pro Ser Ser Tyr Lys Val Ile Leu Gly Ala His Gln Glu Val
    610                 615                 620
```

| | | | | | | | | | | | | | | |
|---|---|---|---|---|---|---|---|---|---|---|---|---|---|---|
| Asn | Leu | Glu | Pro | His | Val | Gln | Glu | Ile | Glu | Val | Ser | Arg | Leu | Phe | Leu |
| 625 | | | | | 630 | | | | | 635 | | | | | 640 |

| | | | | | | | | | | | | | | |
|---|---|---|---|---|---|---|---|---|---|---|---|---|---|---|
| Glu | Pro | Thr | Arg | Lys | Asp | Ile | Ala | Leu | Leu | Lys | Leu | Ser | Ser | Pro | Ala |
| | | | 645 | | | | | 650 | | | | | 655 | | |

| | | | | | | | | | | | | | | |
|---|---|---|---|---|---|---|---|---|---|---|---|---|---|---|
| Val | Ile | Thr | Asp | Lys | Val | Ile | Pro | Ala | Cys | Leu | Pro | Ser | Pro | Asn | Tyr |
| | | | 660 | | | | | 665 | | | | | 670 | | |

| | | | | | | | | | | | | | | |
|---|---|---|---|---|---|---|---|---|---|---|---|---|---|---|
| Val | Val | Ala | Asp | Arg | Thr | Glu | Cys | Phe | Ile | Thr | Gly | Trp | Gly | Glu | Thr |
| | | 675 | | | | | 680 | | | | | 685 | | | |

| | | | | | | | | | | | | | | |
|---|---|---|---|---|---|---|---|---|---|---|---|---|---|---|
| Gln | Gly | Thr | Phe | Gly | Ala | Gly | Leu | Leu | Lys | Glu | Ala | Gln | Leu | Pro | Val |
| | 690 | | | | | 695 | | | | | 700 | | | | |

| | | | | | | | | | | | | | | |
|---|---|---|---|---|---|---|---|---|---|---|---|---|---|---|
| Ile | Glu | Asn | Lys | Val | Cys | Asn | Arg | Tyr | Glu | Phe | Leu | Asn | Gly | Arg | Val |
| 705 | | | | | 710 | | | | | 715 | | | | | 720 |

| | | | | | | | | | | | | | | |
|---|---|---|---|---|---|---|---|---|---|---|---|---|---|---|
| Gln | Ser | Thr | Glu | Leu | Cys | Ala | Gly | His | Leu | Ala | Gly | Gly | Thr | Asp | Ser |
| | | | | 725 | | | | | 730 | | | | | 735 | |

| | | | | | | | | | | | | | | |
|---|---|---|---|---|---|---|---|---|---|---|---|---|---|---|
| Cys | Gln | Gly | Asp | Ser | Gly | Gly | Pro | Leu | Val | Cys | Phe | Glu | Lys | Asp | Lys |
| | | | 740 | | | | | 745 | | | | | 750 | | |

| | | | | | | | | | | | | | |
|---|---|---|---|---|---|---|---|---|---|---|---|---|---|
| Tyr | Ile | Leu | Gln | Gly | Val | Thr | Ser | Trp | Gly | Leu | Gly | Cys | Ala | Arg | Pro |
| | | 755 | | | | | 760 | | | | | 765 | | | |

| | | | | | | | | | | | | | | |
|---|---|---|---|---|---|---|---|---|---|---|---|---|---|---|
| Asn | Lys | Pro | Gly | Val | Tyr | Val | Arg | Val | Ser | Arg | Phe | Val | Thr | Trp | Ile |
| 770 | | | | | 775 | | | | | 780 | | | | | |

| | | | | |
|---|---|---|---|---|
| Glu | Gly | Val | Met | Arg | Asn | Asn |
| 785 | | | | 790 | | |

<210> SEQ ID NO 3
<211> LENGTH: 2433
<212> TYPE: DNA
<213> ORGANISM: Artificial sequence
<220> FEATURE:
<223> OTHER INFORMATION: nucleotide sequence coding for the natural
      plasminogen (from swiss prot)with the signal peptide

<400> SEQUENCE: 3

| | | |
|---|---|---|
| atggaacata aggaagtggt tcttctactt ctttttatttc tgaaatcagg tcaaggagag | 60 |
| cctctggatg actatgtgaa tacccagggg gcttcactgt tcagtgtcac taagaagcag | 120 |
| ctgggagcag aagtatagaa gaatgtgcaa gcaaaatgtg aggaggacga agaattcacc | 180 |
| tgcagggcat tccaatatca cagtaaagag caacaatgtg tgataatggc tgaaaacagg | 240 |
| aagtcctcca taatcattag gatgagagat gtagttttat ttgaaaagaa agtgtatctc | 300 |
| tcagagtgca agactgggaa tggaagaaac tacagaggga cgatgtccaa acaaaaaaat | 360 |
| ggcatcacct gtcaaaaatg gagttccact tctccccaca gacctagatt ctcacctgct | 420 |
| acacacccct cagagggact ggaggagaac tactgcagga tccagacaa cgatccgcag | 480 |
| gggccctggt gctatactac tgatccagaa aagagatatg actactgcga cattcttgag | 540 |
| tgtgaagagg aatgtatgca ttgcagtgga gaaaactatg acggcaaaat ttccaagacc | 600 |
| atgtctggac tggaatgcca ggcctggac tctcagagcc acacgctca tggatacatt | 660 |
| ccttccaaat ttccaaacaa gaacctgaag aagaattact gtcgtaaccc cgataggag | 720 |
| ctgcggcctt ggtgtttcac caccgacccc aacaagcgct gggaactttg tgacatcccc | 780 |
| cgctgcacaa cacctccacc atcttctggt cccaccctacc agtgtctgaa gggaacaggt | 840 |
| gaaaactatc gcgggaatgt ggctgttacc gtgtccgggc acacctgtca gcactggagt | 900 |
| gcacagaccc ctcacacaca taacaggaca ccagaaaact tcccctgcaa aaatttggat | 960 |
| gaaaactact gccgcaatcc tgacggaaaa agggcccat ggtgccatac aaccaacagc | 1020 |
| caagtgcggt gggagtactg taagataccg tcctgtgact cctcccagt atccacggaa | 1080 |

```
caattggctc ccacagcacc acctgagcta acccctgtgg tccaggactg ctaccatggt    1140
gatggacaga gctaccgagg cacatcctcc accaccacca caggaaagaa gtgtcagtct    1200
tggtcatcta tgacaccaca ccggcaccag aagacccag aaaactaccc aaatgctggc    1260
ctgacaatga actactgcag gaatccagat gccgataaag cccctggtg ttttaccaca    1320 gaccccagcg tcaggtggga gtactgcaac ctgaaaaat gctcaggaac agaagcgagt    1380
gttgtagcac ctccgcctgt tgtcctgctt ccagatgtag agactccttc cgaagaagac    1440
tgtatgtttg ggaatgggaa aggataccga ggcaagaggg cgaccactgt tactgggacg    1500
ccatgccagg actgggctgc ccaggagccc atagacaca gcattttcac tccagagaca    1560
aatccacggg cgggtctgga aaaaaattac tgccgtaacc ctgatggtga tgtaggtggt    1620
ccctggtgct acacgacaaa tccaagaaaa ctttacgact actgtgatgt ccctcagtgt    1680 gcggccccctt catttgattg tgggaagcct caagtggagc cgaagaaatg tcctggaagg    1740
gttgtagggg ggtgtgtggc ccacccacat tcctggccct ggcaagtcag tcttagaaca    1800
aggtttggaa tgcacttctg tggaggcacc ttgatatccc cagagtgggt gttgactgct    1860
gcccactgct tggagaagtc cccaaggcct tcatcctaca aggtcatcct gggtgcacac    1920
caagaagtga atctcgaacc gcatgttcag gaaatagaag tgtctaggct gttcttggag    1980
cccacacgaa aagatattgc cttgctaaag ctaagcagtc ctgccgtcat cactgacaaa    2040
gtaatcccag cttgtctgcc atccccaaat tatgtggtcg ctgaccggac cgaatgtttc    2100
atcactggct ggggagaaac ccaaggtact tttggagctg gccttctcaa ggaagcccag    2160
ctccctgtga ttgagaataa agtgtgcaat cgctatgagt ttctgaatgg aagagtccaa    2220
tccaccgaac tctgtgctgg gcatttggcc ggaggcactg acagttgcca gggtgacagt    2280
ggaggtcctc tggtttgctt cgagaaggac aaatacattt tacaaggagt cacttcttgg    2340
ggtcttggct gtgcacgccc caataagcct ggtgtctatg ttcgtgtttc aaggtttgtt    2400
acttggattg agggagtgat gagaaataat taa                                2433
```

<210> SEQ ID NO 4
<211> LENGTH: 810
<212> TYPE: PRT
<213> ORGANISM: Artificial sequence
<220> FEATURE:
<223> OTHER INFORMATION: amino acid sequence coding for the natural
      plasminogen (from swiss prot)with the signal peptide

<400> SEQUENCE: 4

```
Met Glu His Lys Glu Val Val Leu Leu Leu Leu Phe Leu Lys Ser
1               5                   10                  15

Gly Gln Gly Glu Pro Leu Asp Asp Tyr Val Asn Thr Gln Gly Ala Ser
            20                  25                  30

Leu Phe Ser Val Thr Lys Lys Gln Leu Gly Ala Gly Ser Ile Glu Glu
        35                  40                  45

Cys Ala Ala Lys Cys Glu Glu Asp Glu Glu Phe Thr Cys Arg Ala Phe
    50                  55                  60

Gln Tyr His Ser Lys Glu Gln Gln Cys Val Ile Met Ala Glu Asn Arg
65                  70                  75                  80

Lys Ser Ser Ile Ile Ile Arg Met Arg Asp Val Val Leu Phe Glu Lys
                85                  90                  95

Lys Val Tyr Leu Ser Glu Cys Lys Thr Gly Asn Gly Lys Asn Tyr Arg
            100                 105                 110
```

```
Gly Thr Met Ser Lys Thr Lys Asn Gly Ile Thr Cys Gln Lys Trp Ser
            115                 120                 125

Ser Thr Ser Pro His Arg Pro Arg Phe Ser Pro Ala Thr His Pro Ser
        130                 135                 140

Glu Gly Leu Glu Glu Asn Tyr Cys Arg Asn Pro Asp Asn Asp Pro Gln
145                 150                 155                 160

Gly Pro Trp Cys Tyr Thr Thr Asp Pro Glu Lys Arg Tyr Asp Tyr Cys
                165                 170                 175

Asp Ile Leu Glu Cys Glu Glu Cys Met His Cys Ser Gly Glu Asn
            180                 185                 190

Tyr Asp Gly Lys Ile Ser Lys Thr Met Ser Gly Leu Glu Cys Gln Ala
                195                 200                 205

Trp Asp Ser Gln Ser Pro His Ala His Gly Tyr Ile Pro Ser Lys Phe
    210                 215                 220

Pro Asn Lys Asn Leu Lys Lys Asn Tyr Cys Arg Asn Pro Asp Arg Glu
225                 230                 235                 240

Leu Arg Pro Trp Cys Phe Thr Thr Asp Pro Asn Lys Arg Trp Glu Leu
                245                 250                 255

Cys Asp Ile Pro Arg Cys Thr Thr Pro Pro Ser Ser Gly Pro Thr
            260                 265                 270

Tyr Gln Cys Leu Lys Gly Thr Gly Glu Asn Tyr Arg Gly Asn Val Ala
                275                 280                 285

Val Thr Val Ser Gly His Thr Cys Gln His Trp Ser Ala Gln Thr Pro
            290                 295                 300

His Thr His Asn Arg Thr Pro Glu Asn Phe Pro Cys Lys Asn Leu Asp
305                 310                 315                 320

Glu Asn Tyr Cys Arg Asn Pro Asp Gly Lys Arg Ala Pro Trp Cys His
                325                 330                 335

Thr Thr Asn Ser Gln Val Arg Trp Glu Tyr Cys Lys Ile Pro Ser Cys
            340                 345                 350

Asp Ser Ser Pro Val Ser Thr Glu Gln Leu Ala Pro Thr Ala Pro Pro
        355                 360                 365

Glu Leu Thr Pro Val Val Gln Asp Cys Tyr His Gly Asp Gly Gln Ser
        370                 375                 380

Tyr Arg Gly Thr Ser Ser Thr Thr Thr Gly Lys Lys Cys Gln Ser
385                 390                 395                 400

Trp Ser Ser Met Thr Pro His Arg His Gln Lys Thr Pro Glu Asn Tyr
                405                 410                 415

Pro Asn Ala Gly Leu Thr Met Asn Tyr Cys Arg Asn Pro Asp Ala Asp
                420                 425                 430

Lys Gly Pro Trp Cys Phe Thr Thr Asp Pro Ser Val Arg Trp Glu Tyr
                435                 440                 445

Cys Asn Leu Lys Lys Cys Ser Gly Thr Glu Ala Ser Val Val Ala Pro
            450                 455                 460

Pro Pro Val Val Leu Leu Pro Asp Val Glu Thr Pro Ser Glu Glu Asp
465                 470                 475                 480

Cys Met Phe Gly Asn Gly Lys Gly Tyr Arg Gly Lys Arg Ala Thr Thr
                485                 490                 495

Val Thr Gly Thr Pro Cys Gln Asp Trp Ala Ala Gln Glu Pro His Arg
            500                 505                 510

His Ser Ile Phe Thr Pro Glu Thr Asn Pro Arg Ala Gly Leu Glu Lys
        515                 520                 525
```

```
Asn Tyr Cys Arg Asn Pro Asp Gly Asp Val Gly Gly Pro Trp Cys Tyr
        530                 535                 540

Thr Thr Asn Pro Arg Lys Leu Tyr Asp Tyr Cys Asp Val Pro Gln Cys
545                 550                 555                 560

Ala Ala Pro Ser Phe Asp Cys Gly Lys Pro Gln Val Glu Pro Lys Lys
                565                 570                 575

Cys Pro Gly Arg Val Val Gly Gly Cys Val Ala His Pro His Ser Trp
                580                 585                 590

Pro Trp Gln Val Ser Leu Arg Thr Arg Phe Gly Met His Phe Cys Gly
            595                 600                 605

Gly Thr Leu Ile Ser Pro Glu Trp Val Leu Thr Ala Ala His Cys Leu
            610                 615                 620

Glu Lys Ser Pro Arg Pro Ser Ser Tyr Lys Val Ile Leu Gly Ala His
625                 630                 635                 640

Gln Glu Val Asn Leu Glu Pro His Val Gln Glu Ile Glu Val Ser Arg
                645                 650                 655

Leu Phe Leu Glu Pro Thr Arg Lys Asp Ile Ala Leu Leu Lys Leu Ser
                660                 665                 670

Ser Pro Ala Val Ile Thr Asp Lys Val Ile Pro Ala Cys Leu Pro Ser
            675                 680                 685

Pro Asn Tyr Val Val Ala Asp Arg Thr Glu Cys Phe Ile Thr Gly Trp
            690                 695                 700

Gly Glu Thr Gln Gly Thr Phe Gly Ala Gly Leu Leu Lys Glu Ala Gln
705                 710                 715                 720

Leu Pro Val Ile Glu Asn Lys Val Cys Asn Arg Tyr Glu Phe Leu Asn
                725                 730                 735

Gly Arg Val Gln Ser Thr Glu Leu Cys Ala Gly His Leu Ala Gly Gly
                740                 745                 750

Thr Asp Ser Cys Gln Gly Asp Ser Gly Gly Pro Leu Val Cys Phe Glu
            755                 760                 765

Lys Asp Lys Tyr Ile Leu Gln Gly Val Thr Ser Trp Gly Leu Gly Cys
770                 775                 780

Ala Arg Pro Asn Lys Pro Gly Val Tyr Val Arg Val Ser Arg Phe Val
785                 790                 795                 800

Thr Trp Ile Glu Gly Val Met Arg Asn Asn
                805                 810

<210> SEQ ID NO 5
<211> LENGTH: 2145
<212> TYPE: DNA
<213> ORGANISM: Artificial sequence
<220> FEATURE:
<223> OTHER INFORMATION: nucleotide sequence coding for LYS77-PLG(Lys-
      plasminogen)

<400> SEQUENCE: 5
aaagtgtatc tctcagagtg caagactggg aatggaaaga actacagagg gacgatgtcc    60
aaaacaaaaa atggcatcac ctgtcaaaaa tggagttcca cttctcccca cagacctaga   120
ttctcacctg ctacacaccc ctcagaggga ctggaggaga actactgcag gaatccagac   180
aacgatccgc aggggccctg gtgctatact actgatccag aaaagagata tgactactgc   240
gacattcttg agtgtgaaga ggaatgtatg cattgcagtg agaaaactga tgacggcaaa   300
atttccaaga ccatgtctgg actggaatgc caggcctggg actctcagag cccacacgct   360
catggataca ttccttccaa atttccaaac aagaacctga agaagaatta ctgtcgtaac   420
```

```
cccgataggg agctgcggcc ttggtgtttc accaccgacc ccaacaagcg ctgggaactt    480
tgtgacatcc cccgctgcac aacacctcca ccatcttctg gtcccaccta ccagtgtctg    540
aagggaacag gtgaaaacta tcgcgggaat gtggctgtta ccgtgtccgg gcacacctgt    600
cagcactgga gtgcacagac ccctcacaca cataacagga caccagaaaa cttcccctgc    660
aaaaatttgg atgaaaacta ctgccgcaat cctgacggaa aaggggcccc atggtgccat    720
acaaccaaca gccaagtgcg gtgggagtac tgtaagatac cgtcctgtga ctcctcccca    780
gtatccacgg aacaattggc tcccacagca ccacctgagc taaccccgt ggtccaggac    840 tgctaccatg gtgatggaca gagctaccga ggcacatcct ccaccaccac acaggaaag    900 aagtgtcagt cttggtcatc tatgacacca caccggcacc agaagacccc agaaaactac    960
ccaaatgctg gcctgacaat gaactactgc aggaatccag atgccgataa aggcccctgg   1020
tgttttacca cagaccccag cgtcaggtgg gagtactgca acctgaaaaa atgctcagga   1080
acagaagcga gtgttgtagc acctccgcct gttgtcctgc ttccagatgt agagactcct   1140
tccgaagaag actgtatgtt tgggaatggg aaaggatacc gaggcaagag ggcgaccact   1200
gttactggga cgccatgcca ggactgggct gcccaggagc ccatagaca cagcattttc   1260 actccagaga caaatccacg ggcgggtctg gaaaaaaatt actgccgtaa ccctgatggt   1320
gatgtaggtg gtccctggtg ctacacgaca aatccaagaa aactttacga ctactgtgat   1380
gtccctcagt gtgcggcccc ttcatttgat tgtgggaagc ctcaagtgga gccgaagaaa   1440
tgtcctggaa gggttgtagg ggggtgtgtg gcccacccac attcctggcc ctggcaagtc   1500
agtcttagaa caaggtttgg aatgcacttc tgtggaggca ccttgatatc cccagagtgg   1560
gtgttgactg ctgcccactg cttggagaag tccccaaggc cttcatccta caaggtcatc   1620
ctgggtgcac accaagaagt gaatctcgaa ccgcatgttc aggaaataga agtgtctagg   1680
ctgttcttgg agcccacacg aaaagatatt gccttgctaa agctaagcag tcctgccgtc   1740
atcactgaca aagtaatccc agcttgtctg ccatccccaa attatgtggt cgctgaccgg   1800
accgaatgtt tcatcactgg ctggggagaa acccaaggta cttttggagc tggccttctc   1860
aaggaagccc agctccctgt gattgagaat aaagtgtgca atcgctatga gtttctgaat   1920
ggaagagtcc aatccaccga actctgtgct gggcatttgg ccggaggcac tgacagttgc   1980
cagggtgaca gtggaggtcc tctggttgc ttcgagaagg acaaatacat tttacaagga   2040
gtcacttctt ggggtcttgg ctgtgcacgc cccaataagc ctggtgtcta tgttcgtgtt   2100
tcaaggtttg ttacttggat tgagggagtg atgagaaata attaa                  2145
```

<210> SEQ ID NO 6
<211> LENGTH: 714
<212> TYPE: PRT
<213> ORGANISM: Artificial sequence
<220> FEATURE:
<223> OTHER INFORMATION: amino acid sequence of LYS77-PLG(Lys-plasminogen)

<400> SEQUENCE: 6

Lys Val Tyr Leu Ser Glu Cys Lys Thr Gly Asn Gly Lys Asn Tyr Arg
1               5                   10                  15

Gly Thr Met Ser Lys Thr Lys Asn Gly Ile Thr Cys Gln Lys Trp Ser
            20                  25                  30

Ser Thr Ser Pro His Arg Pro Arg Phe Ser Pro Ala Thr His Pro Ser
        35                  40                  45

-continued

```
Glu Gly Leu Glu Glu Asn Tyr Cys Arg Asn Pro Asp Asn Asp Pro Gln
     50                  55                  60
Gly Pro Trp Cys Tyr Thr Thr Asp Pro Glu Lys Arg Tyr Asp Tyr Cys
 65                  70                  75                  80
Asp Ile Leu Glu Cys Glu Glu Cys Met His Cys Ser Gly Glu Asn
                 85                  90                  95
Tyr Asp Gly Lys Ile Ser Lys Thr Met Ser Gly Leu Glu Cys Gln Ala
            100                 105                 110
Trp Asp Ser Gln Ser Pro His Ala His Gly Tyr Ile Pro Ser Lys Phe
            115                 120                 125
Pro Asn Lys Asn Leu Lys Lys Asn Tyr Cys Arg Asn Pro Asp Arg Glu
            130                 135                 140
Leu Arg Pro Trp Cys Phe Thr Thr Asp Pro Asn Lys Arg Trp Glu Leu
145                 150                 155                 160
Cys Asp Ile Pro Arg Cys Thr Thr Pro Pro Ser Ser Gly Pro Thr
                165                 170                 175
Tyr Gln Cys Leu Lys Gly Thr Gly Glu Asn Tyr Arg Gly Asn Val Ala
            180                 185                 190
Val Thr Val Ser Gly His Thr Cys Gln His Trp Ser Ala Gln Thr Pro
            195                 200                 205
His Thr His Asn Arg Thr Pro Glu Asn Phe Pro Cys Lys Asn Leu Asp
210                 215                 220
Glu Asn Tyr Cys Arg Asn Pro Asp Gly Lys Arg Ala Pro Trp Cys His
225                 230                 235                 240
Thr Thr Asn Ser Gln Val Arg Trp Glu Tyr Cys Lys Ile Pro Ser Cys
            245                 250                 255
Asp Ser Ser Pro Val Ser Thr Glu Gln Leu Ala Pro Thr Ala Pro Pro
            260                 265                 270
Glu Leu Thr Pro Val Val Gln Asp Cys Tyr His Gly Asp Gly Gln Ser
            275                 280                 285
Tyr Arg Gly Thr Ser Ser Thr Thr Thr Thr Gly Lys Lys Cys Gln Ser
290                 295                 300
Trp Ser Ser Met Thr Pro His Arg His Gln Lys Thr Pro Glu Asn Tyr
305                 310                 315                 320
Pro Asn Ala Gly Leu Thr Met Asn Tyr Cys Arg Asn Pro Asp Ala Asp
            325                 330                 335
Lys Gly Pro Trp Cys Phe Thr Thr Asp Pro Ser Val Arg Trp Glu Tyr
            340                 345                 350
Cys Asn Leu Lys Lys Cys Ser Gly Thr Glu Ala Ser Val Val Ala Pro
            355                 360                 365
Pro Pro Val Val Leu Leu Pro Asp Val Glu Thr Pro Ser Glu Glu Asp
            370                 375                 380
Cys Met Phe Gly Asn Gly Lys Gly Tyr Arg Gly Lys Arg Ala Thr Thr
385                 390                 395                 400
Val Thr Gly Thr Pro Cys Gln Asp Trp Ala Ala Gln Glu Pro His Arg
                405                 410                 415
His Ser Ile Phe Thr Pro Glu Thr Asn Pro Arg Ala Gly Leu Glu Lys
            420                 425                 430
Asn Tyr Cys Arg Asn Pro Asp Gly Asp Val Gly Gly Pro Trp Cys Tyr
            435                 440                 445
Thr Thr Asn Pro Arg Lys Leu Tyr Asp Tyr Cys Asp Val Pro Gln Cys
450                 455                 460
```

Ala Ala Pro Ser Phe Asp Cys Gly Lys Pro Gln Val Glu Pro Lys Lys
465                 470                 475                 480

Cys Pro Gly Arg Val Val Gly Gly Cys Val Ala His Pro His Ser Trp
            485                 490                 495

Pro Trp Gln Val Ser Leu Arg Thr Arg Phe Gly Met His Phe Cys Gly
        500                 505                 510

Gly Thr Leu Ile Ser Pro Glu Trp Val Leu Thr Ala Ala His Cys Leu
            515                 520                 525

Glu Lys Ser Pro Arg Pro Ser Ser Tyr Lys Val Ile Leu Gly Ala His
    530                 535                 540

Gln Glu Val Asn Leu Glu Pro His Val Gln Ile Glu Val Ser Arg
545                 550                 555                 560

Leu Phe Leu Glu Pro Thr Arg Lys Asp Ile Ala Leu Leu Lys Leu Ser
                565                 570                 575

Ser Pro Ala Val Ile Thr Asp Lys Val Ile Pro Ala Cys Leu Pro Ser
            580                 585                 590

Pro Asn Tyr Val Val Ala Asp Arg Thr Glu Cys Phe Ile Thr Gly Trp
        595                 600                 605

Gly Glu Thr Gln Gly Thr Phe Gly Ala Gly Leu Leu Lys Glu Ala Gln
    610                 615                 620

Leu Pro Val Ile Glu Asn Lys Val Cys Asn Arg Tyr Glu Phe Leu Asn
625                 630                 635                 640

Gly Arg Val Gln Ser Thr Glu Leu Cys Ala Gly His Leu Ala Gly Gly
                645                 650                 655

Thr Asp Ser Cys Gln Gly Asp Ser Gly Gly Pro Leu Val Cys Phe Glu
            660                 665                 670

Lys Asp Lys Tyr Ile Leu Gln Gly Val Thr Ser Trp Gly Leu Gly Cys
        675                 680                 685

Ala Arg Pro Asn Lys Pro Gly Val Tyr Val Arg Val Ser Arg Phe Val
    690                 695                 700

Thr Trp Ile Glu Gly Val Met Arg Asn Asn
705                 710

<210> SEQ ID NO 7
<211> LENGTH: 1245
<212> TYPE: DNA
<213> ORGANISM: Artificial sequence
<220> FEATURE:
<223> OTHER INFORMATION: nucleotide sequence coding for delta-plg(delta-
      plasminogen)

<400> SEQUENCE: 7
gagcctctgg atgactatgt gaatacccag ggggcttcac tgttcagtgt cactaagaag      60
cagctgggag caggaagtat agaagaatgt gcagcaaaat gtgaggagga cgaagaattc     120
acctgcaggg cattccaata tcacagtaaa gagcaacaat gtgtgataat ggctgaaaac     180
aggaagtcct ccataatcat taggatgaga gatgtagttt tatttgaaaa gaaagtgtat     240
ctctcagagt gcaagactgg gaatggaaag aactacagag gacgatgtc caaaacaaaa     300 aatggcatca cctgtcaaaa atggagttcc acttctcccc acagacctag attctcacct     360
gctacacacc cctcagaggg actggaggag aactactgca ggaatccaga caacgatccg     420
caggggccct ggtgctatac tactgatcca gaaaagagat atgactactg cgacattctt     480
gagtgtgaag aggcggcccc ttcatttgat tgtgggaagc ctcaagtgga gccgaagaaa     540
tgtcctggaa gggttgtagg ggggtgtgtg gcccacccac attcctggcc ctggcaagtc     600

-continued

```
agtcttagaa caaggtttgg aatgcacttc tgtggaggca ccttgatatc cccagagtgg    660
gtgttgactg ctgcccactg cttggagaag tccccaaggc cttcatccta caaggtcatc    720
ctgggtgcac accaagaagt gaatctcgaa ccgcatgttc aggaaataga agtgtctagg    780
ctgttcttgg agcccacacg aaaagatatt gccttgctaa agctaagcag tcctgccgtc    840
atcactgaca agtaatccc agcttgtctg ccatccccaa attatgtggt cgctgaccgg    900
accgaatgtt tcatcactgg ctggggagaa acccaaggta cttttggagc tggccttctc    960
aaggaagccc agctccctgt gattgagaat aaagtgtgca atcgctatga gtttctgaat   1020
ggaagagtcc aatccaccga actctgtgct gggcatttgg ccggaggcac tgacagttgc   1080
cagggtgaca gtggaggtcc tctggtttgc ttcgagaagg acaaatacat tttacaagga   1140
gtcacttctt ggggtcttgg ctgtgcacgc cccaataagc ctggtgtcta tgttcgtgtt   1200
tcaaggtttg ttacttggat tgagggagtg atgagaaata attaa                  1245
```

<210> SEQ ID NO 8
<211> LENGTH: 414
<212> TYPE: PRT
<213> ORGANISM: Artificial sequence
<220> FEATURE:
<223> OTHER INFORMATION: amino acid sequence of delta-plg(delta-plasminogen)

<400> SEQUENCE: 8

```
Glu Pro Leu Asp Asp Tyr Val Asn Thr Gln Gly Ala Ser Leu Phe Ser
1               5                   10                  15

Val Thr Lys Lys Gln Leu Gly Ala Gly Ser Ile Glu Glu Cys Ala Ala
            20                  25                  30

Lys Cys Glu Glu Asp Glu Glu Phe Thr Cys Arg Ala Phe Gln Tyr His
        35                  40                  45

Ser Lys Glu Gln Gln Cys Val Ile Met Ala Glu Asn Arg Lys Ser Ser
    50                  55                  60

Ile Ile Ile Arg Met Arg Asp Val Val Leu Phe Glu Lys Lys Val Tyr
65                  70                  75                  80

Leu Ser Glu Cys Lys Thr Gly Asn Gly Lys Asn Tyr Arg Gly Thr Met
                85                  90                  95

Ser Lys Thr Lys Asn Gly Ile Thr Cys Gln Lys Trp Ser Ser Thr Ser
            100                 105                 110

Pro His Arg Pro Arg Phe Ser Pro Ala Thr His Pro Ser Glu Gly Leu
        115                 120                 125

Glu Glu Asn Tyr Cys Arg Asn Pro Asp Asn Asp Pro Gln Gly Pro Trp
    130                 135                 140

Cys Tyr Thr Thr Asp Pro Glu Lys Arg Tyr Asp Tyr Cys Asp Ile Leu
145                 150                 155                 160

Glu Cys Glu Glu Ala Ala Pro Ser Phe Asp Cys Gly Lys Pro Gln Val
                165                 170                 175

Glu Pro Lys Lys Cys Pro Gly Arg Val Val Gly Gly Cys Val Ala His
            180                 185                 190

Pro His Ser Trp Pro Trp Gln Val Ser Leu Arg Thr Arg Phe Gly Met
        195                 200                 205

His Phe Cys Gly Gly Thr Leu Ile Ser Pro Glu Trp Val Leu Thr Ala
    210                 215                 220

Ala His Cys Leu Glu Lys Ser Pro Arg Pro Ser Ser Tyr Lys Val Ile
225                 230                 235                 240
```

```
Leu Gly Ala His Gln Glu Val Asn Leu Glu Pro His Val Gln Glu Ile
            245                 250                 255

Glu Val Ser Arg Leu Phe Leu Glu Pro Thr Arg Lys Asp Ile Ala Leu
        260                 265                 270

Leu Lys Leu Ser Ser Pro Ala Val Ile Thr Asp Lys Val Ile Pro Ala
    275                 280                 285

Cys Leu Pro Ser Pro Asn Tyr Val Val Ala Asp Arg Thr Glu Cys Phe
290                 295                 300

Ile Thr Gly Trp Gly Glu Thr Gln Gly Thr Phe Gly Ala Gly Leu Leu
305                 310                 315                 320

Lys Glu Ala Gln Leu Pro Val Ile Glu Asn Lys Val Cys Asn Arg Tyr
            325                 330                 335

Glu Phe Leu Asn Gly Arg Val Gln Ser Thr Glu Leu Cys Ala Gly His
        340                 345                 350

Leu Ala Gly Gly Thr Asp Ser Cys Gln Gly Asp Ser Gly Gly Pro Leu
    355                 360                 365

Val Cys Phe Glu Lys Asp Lys Tyr Ile Leu Gln Gly Val Thr Ser Trp
370                 375                 380

Gly Leu Gly Cys Ala Arg Pro Asn Lys Pro Gly Val Tyr Val Arg Val
385                 390                 395                 400

Ser Arg Phe Val Thr Trp Ile Glu Gly Val Met Arg Asn Asn
            405                 410
```

<210> SEQ ID NO 9
<211> LENGTH: 1104
<212> TYPE: DNA
<213> ORGANISM: Artificial sequence
<220> FEATURE:
<223> OTHER INFORMATION: nucleotide sequence coding for Mini-plg(mini-plasminogen)

<400> SEQUENCE: 9

```
gtcaggtggg agtactgcaa cctgaaaaaa tgctcaggaa cagaagcgag tgttgtagca      60
cctccgcctg ttgtcctgct tccagatgta gagactcctt ccgaagaaga ctgtatgttt     120
gggaatggga aaggataccg aggcaagagg gcgaccactg ttactgggac gccatgccag     180
gactgggctg cccaggagcc ccatagacac agcattttca ctccagagac aaatccacgg     240
gcgggtctgg aaaaaaatta ctgccgtaac cctgatggtg atgtaggtgg tccctggtgc     300
tacacgacaa atccaagaaa actttacgac tactgtgatg tccctcagtg tgcggcccct     360
tcatttgatt gtgggaagcc tcaagtggag ccgaagaaat gtcctggaag ggttgtaggg     420
gggtgtgtgg cccacccaca ttcctggccc tggcaagtca gtcttagaac aaggtttgga     480
atgcacttct gtggaggcac cttgatatcc ccagagtggg tgttgactgc tgcccactgc     540
ttggagaagt cccaaggcc ttcatcctac aaggtcatcc tgggtgcaca ccaagaagtg     600
aatctcgaac cgcatgttca ggaaatagaa gtgtctaggc tgttcttgga gcccacacga     660
aaagatattg ccttgctaaa gctaagcagt cctgccgtca tcactgacaa agtaatccca     720
gcttgtctgc catccccaaa ttatgtggtc gctgaccgga ccgaatgttt catcactggc     780
tggggagaaa cccaaggtac ttttggagct ggccttctca ggaagcccca gctccctgtg     840
attgagaata agtgtgcaa tcgctatgag tttctgaatg gaagagtcca atccaccgaa     900
ctctgtgctg gcatttggc cggaggcact gacagttgcc agggtgacag tggaggtcct     960
ctggtttgct tcgagaagga caaatacatt ttacaaggag tcacttcttg gggtcttggc    1020
```

```
tgtgcacgcc ccaataagcc tggtgtctat gttcgtgttt caaggtttgt tacttggatt   1080
gagggagtga tgagaaataa ttaa                                          1104
```

<210> SEQ ID NO 10
<211> LENGTH: 367
<212> TYPE: PRT
<213> ORGANISM: Artificial sequence
<220> FEATURE:
<223> OTHER INFORMATION: amino acid sequence of Mini-plg(mini-plasminogen)

<400> SEQUENCE: 10

```
Val Arg Trp Glu Tyr Cys Asn Leu Lys Lys Cys Ser Gly Thr Glu Ala
1               5                   10                  15

Ser Val Val Ala Pro Pro Val Val Leu Leu Pro Asp Val Glu Thr
            20                  25                  30

Pro Ser Glu Glu Asp Cys Met Phe Gly Asn Gly Lys Gly Tyr Arg Gly
        35                  40                  45

Lys Arg Ala Thr Thr Val Thr Gly Thr Pro Cys Gln Asp Trp Ala Ala
    50                  55                  60

Gln Glu Pro His Arg His Ser Ile Phe Thr Pro Glu Thr Asn Pro Arg
65                  70                  75                  80

Ala Gly Leu Glu Lys Asn Tyr Cys Arg Asn Pro Asp Gly Asp Val Gly
                85                  90                  95

Gly Pro Trp Cys Tyr Thr Thr Asn Pro Arg Lys Leu Tyr Asp Tyr Cys
            100                 105                 110

Asp Val Pro Gln Cys Ala Ala Pro Ser Phe Asp Cys Gly Lys Pro Gln
        115                 120                 125

Val Glu Pro Lys Lys Cys Pro Gly Arg Val Val Gly Gly Cys Val Ala
    130                 135                 140

His Pro His Ser Trp Pro Trp Gln Val Ser Leu Arg Thr Arg Phe Gly
145                 150                 155                 160

Met His Phe Cys Gly Gly Thr Leu Ile Ser Pro Glu Trp Val Leu Thr
                165                 170                 175

Ala Ala His Cys Leu Glu Lys Ser Pro Arg Pro Ser Ser Tyr Lys Val
            180                 185                 190

Ile Leu Gly Ala His Gln Glu Val Asn Leu Glu Pro His Val Gln Glu
        195                 200                 205

Ile Glu Val Ser Arg Leu Phe Leu Glu Pro Thr Arg Lys Asp Ile Ala
    210                 215                 220

Leu Leu Lys Leu Ser Ser Pro Ala Val Ile Thr Asp Lys Val Ile Pro
225                 230                 235                 240

Ala Cys Leu Pro Ser Pro Asn Tyr Val Val Ala Asp Arg Thr Glu Cys
                245                 250                 255

Phe Ile Thr Gly Trp Gly Glu Thr Gln Gly Thr Phe Gly Ala Gly Leu
            260                 265                 270

Leu Lys Glu Ala Gln Leu Pro Val Ile Glu Asn Lys Val Cys Asn Arg
        275                 280                 285

Tyr Glu Phe Leu Asn Gly Arg Val Gln Ser Thr Glu Leu Cys Ala Gly
    290                 295                 300

His Leu Ala Gly Gly Thr Asp Ser Cys Gln Gly Asp Ser Gly Gly Pro
305                 310                 315                 320

Leu Val Cys Phe Glu Lys Asp Lys Tyr Ile Leu Gln Gly Val Thr Ser
                325                 330                 335
```

```
Trp Gly Leu Gly Cys Ala Arg Pro Asn Lys Pro Gly Val Tyr Val Arg
                340                 345                 350

Val Ser Arg Phe Val Thr Trp Ile Glu Gly Val Met Arg Asn Asn
        355                 360                 365
```

<210> SEQ ID NO 11
<211> LENGTH: 750
<212> TYPE: DNA
<213> ORGANISM: Artificial sequence
<220> FEATURE:
<223> OTHER INFORMATION: nucleotide sequence coding for Micro-plg(micro-plasminogen)

<400> SEQUENCE: 11

```
gccccttcat tgattgtgg gaagcctcaa gtggagccga agaaatgtcc tggaagggtt      60
gtagggggggt gtgtggccca cccacattcc tggccctggc aagtcagtct tagaacaagg    120
tttggaatgc acttctgtgg aggcaccttg atatcccag agtgggtgtt gactgctgcc     180
cactgcttgg agaagtcccc aaggccttca tcctacaagg tcatcctggg tgcacaccaa    240
gaagtgaatc tcgaaccgca tgttcaggaa atagaagtgt ctaggctgtt cttggagccc    300
acacgaaaag atattgcctt gctaaagcta agcagtcctg ccgtcatcac tgacaaagta    360
atcccagctt gtctgccatc cccaaattat gtggtcgctg accggaccga atgtttcatc    420
actggctggg gagaaaccca aggtactttt ggagctggcc ttctcaagga agcccagctc    480
cctgtgattg agaataaagt gtgcaatcgc tatgagtttc tgaatggaag agtccaatcc    540
accgaactct gtgctgggca tttggccgga ggcactgaca gttgccaggg tgacagtgga    600
ggtcctctgg tttgcttcga gaaggacaaa tacattttac aaggagtcac ttcttggggt    660
cttggctgtg cacgccccaa taagcctggt gtctatgttc gtgtttcaag gtttgttact    720
tggattgagg gagtgatgag aaataattaa                                     750
```

<210> SEQ ID NO 12
<211> LENGTH: 249
<212> TYPE: PRT
<213> ORGANISM: Artificial sequence
<220> FEATURE:
<223> OTHER INFORMATION: amino acid sequence coding for Micro-plg(micro-plasminogen)

<400> SEQUENCE: 12

```
Ala Pro Ser Phe Asp Cys Gly Lys Pro Gln Val Glu Pro Lys Lys Cys
  1               5                  10                  15

Pro Gly Arg Val Val Gly Gly Cys Val Ala His Pro His Ser Trp Pro
                20                  25                  30

Trp Gln Val Ser Leu Arg Thr Arg Phe Gly Met His Phe Cys Gly Gly
            35                  40                  45

Thr Leu Ile Ser Pro Glu Trp Val Leu Thr Ala Ala His Cys Leu Glu
        50                  55                  60

Lys Ser Pro Arg Pro Ser Ser Tyr Lys Val Ile Leu Gly Ala His Gln
 65                  70                  75                  80

Glu Val Asn Leu Glu Pro His Val Gln Glu Ile Glu Val Ser Arg Leu
                85                  90                  95

Phe Leu Glu Pro Thr Arg Lys Asp Ile Ala Leu Leu Lys Leu Ser Ser
            100                 105                 110

Pro Ala Val Ile Thr Asp Lys Val Ile Pro Ala Cys Leu Pro Ser Pro
        115                 120                 125
```

Asn Tyr Val Val Ala Asp Arg Thr Glu Cys Phe Ile Thr Gly Trp Gly
            130                 135                 140

Glu Thr Gln Gly Thr Phe Gly Ala Gly Leu Leu Lys Glu Ala Gln Leu
145                 150                 155                 160

Pro Val Ile Glu Asn Lys Val Cys Asn Arg Tyr Glu Phe Leu Asn Gly
                165                 170                 175

Arg Val Gln Ser Thr Glu Leu Cys Ala Gly His Leu Ala Gly Gly Thr
            180                 185                 190

Asp Ser Cys Gln Gly Asp Ser Gly Gly Pro Leu Val Cys Phe Glu Lys
            195                 200                 205

Asp Lys Tyr Ile Leu Gln Gly Val Thr Ser Trp Gly Leu Gly Cys Ala
            210                 215                 220

Arg Pro Asn Lys Pro Gly Val Tyr Val Arg Val Ser Arg Phe Val Thr
225                 230                 235                 240

Trp Ile Glu Gly Val Met Arg Asn Asn
                245

<210> SEQ ID NO 13
<211> LENGTH: 684
<212> TYPE: DNA
<213> ORGANISM: Artificial sequence
<220> FEATURE:
<223> OTHER INFORMATION: nucleotide sequence coding for the serine
      protease domain

<400> SEQUENCE: 13
gttgtagggg ggtgtgtggc ccacccacat tcctggccct ggcaagtcag tcttagaaca      60
aggtttggaa tgcacttctg tggaggcacc ttgatatccc agagtgggt gttgactgct      120 gcccactgct tggagaagtc cccaaggcct tcatcctaca aggtcatcct gggtgcacac     180
caagaagtga atctcgaacc gcatgttcag gaaatagaag tgtctaggct gttcttggag     240
cccacacgaa aagatattgc cttgctaaag ctaagcagtc ctgccgtcat cactgacaaa     300
gtaatcccag cttgtctgcc atccccaaat tatgtggtcg ctgaccggac cgaatgtttc     360
atcactggct ggggagaaac ccaaggtact tttggagctg gccttctcaa ggaagcccag     420
ctccctgtga ttgagaataa agtgtgcaat cgctatgagt ttctgaatgg aagagtccaa     480
tccaccgaac tctgtgctgg gcatttggcc ggaggcactg acagttgcca gggtgacagt     540
ggaggtcctc tggtttgctt cgagaaggac aaatacattt tacaaggagt cacttcttgg     600
ggtcttggct gtgcacgccc caataagcct ggtgtctatg ttcgtgtttc aaggtttgtt     660
acttggattg agggagtgat gaga                                            684

<210> SEQ ID NO 14
<211> LENGTH: 228
<212> TYPE: PRT
<213> ORGANISM: Artificial sequence
<220> FEATURE:
<223> OTHER INFORMATION: amino acid sequence coding for the serine
      protease domain

<400> SEQUENCE: 14

Val Val Gly Gly Cys Val Ala His Pro His Ser Trp Pro Trp Gln Val
1               5                   10                  15

Ser Leu Arg Thr Arg Phe Gly Met His Phe Cys Gly Gly Thr Leu Ile
            20                  25                  30

Ser Pro Glu Trp Val Leu Thr Ala Ala His Cys Leu Glu Lys Ser Pro
        35                  40                  45

-continued

```
Arg Pro Ser Ser Tyr Lys Val Ile Leu Gly Ala His Gln Glu Val Asn
    50              55                  60
Leu Glu Pro His Val Gln Glu Ile Glu Val Ser Arg Leu Phe Leu Glu
65              70                  75                      80
Pro Thr Arg Lys Asp Ile Ala Leu Leu Lys Leu Ser Ser Pro Ala Val
            85                      90              95
Ile Thr Asp Lys Val Ile Pro Ala Cys Leu Pro Ser Pro Asn Tyr Val
            100                 105             110
Val Ala Asp Arg Thr Glu Cys Phe Ile Thr Gly Trp Gly Glu Thr Gln
        115             120                 125
Gly Thr Phe Gly Ala Gly Leu Leu Lys Glu Ala Gln Leu Pro Val Ile
        130             135             140
Glu Asn Lys Val Cys Asn Arg Tyr Glu Phe Leu Asn Gly Arg Val Gln
145             150                 155                     160
Ser Thr Glu Leu Cys Ala Gly His Leu Ala Gly Gly Thr Asp Ser Cys
                165             170                 175
Gln Gly Asp Ser Gly Gly Pro Leu Val Cys Phe Glu Lys Asp Lys Tyr
            180                 185             190
Ile Leu Gln Gly Val Thr Ser Trp Gly Leu Gly Cys Ala Arg Pro Asn
        195             200             205
Lys Pro Gly Val Tyr Val Arg Val Ser Arg Phe Val Thr Trp Ile Glu
    210             215                 220
Gly Val Met Arg
225
```

METHOD AND DRUG FOR PREVENTING OR TREATING OSTEOARTHRITIS

CROSS REFERENCE TO RELATED APPLICATIONS

This application is a National Phase application under 35 U.S.C. § 371 of International Application No. PCT/CN2018/121535, filed Dec. 17, 2018, which claims priority to International Application No. PCT/CN2017/116636, filed Dec. 15, 2017, the contents of each of which are incorporated herein by reference in their entirety.

SUBMISSION OF SEQUENCE LISTING ON ASCII TEXT FILE

The content of the following submission on ASCII text file is incorporated herein by reference in its entirety: a computer readable form (CRF) of the Sequence Listing (file name 794922001800SEQLIST.txt, date recorded: Jun. 15, 2020, size: 46 KB).

FIELD OF THE INVENTION

The present invention relates to a method and a medicament for preventing or treating osteoarthritis by using plasminogen.

BACKGROUND OF THE INVENTION

Osteoarthritis is also known as osteo-arthritis, degenerative arthritis, degenerative joint disease, and osteoarthropathy. It is the most common form of arthritis, affecting about 237 million (3.3%) of the population, and is also one of the leading reasons for joint pain and even disability [1], among people over the age of 60, about 10% of men and 18% of women are affected by it [2]. Osteoarthritis is a heterogeneous disease caused by multiple factors, and is characterized by the progressive breakdown of articular cartilage; these factors include trauma, abnormal mechanical load, inadequate nutrition supply, and genetic causes, as well as metabolic factors and subpatellar fat pad. Previous studies have focused on the impact of abnormal biomechanics on subchondral bone, articular cartilage integrity, and chondrocyte pathophysiology; but recent evidences indicate that the clinical symptoms of osteoarthritis affect not only articular cartilage, but also the integrity of multiple joint tissues, including synovium, bone, ligaments, supporting muscles and meniscus, etc. [3]

The primary cause of osteoarthritis is not a bone lesion. Modern medical research has found that the primary cause of the disease is the loss of joint protection capabilities of the "joint protection systems" such as cartilage. Particularly, the occurrence of various types of osteoarticular diseases often starts from synovial lesions, damaged or degenerated cartilage: cartilage injury caused by taking certain anti-inflammatory and hormonal medicaments is also one of the main causes of many osteoarticular diseases. Due to the damage of joint synovium and cartilage, and the lack of articular synovia, the joint bones lack the necessary protection, so that when the human body is active, the bones at the joints directly suffer from severe hard friction for lacking the necessary "cartilage protection", thereby leading to joint pain, swelling, deformation, bone spur hyperplasia and other symptoms in a patient [4]. Therefore, the key points for treating osteoarticular diseases are to repair damaged articular cartilage and synovium, promoting the regeneration ability of cartilage and synovium, and stimulating articular synovia, thereby restoring the "cartilage protective layer" of joint organs. This study proves that plasminogen can improve the structural integrity of bone joints, enhance the activity of local osteoblasts in a joint, and/or reduce the activity of osteoclasts, promote cartilage regeneration and the bone remodeling of subchondral bone, and effectively relieve pain, etc.: thereby developing a new way for treating joint injury diseases including osteoarthritis.

CONTENTS OF THE INVENTION/SUMMARY OF THE INVENTION

The present invention relates to a method and a medicament for preventing or treating osteoarticular diseases by using plasminogen. The present invention proves that plasminogen can improve the structural integrity of bone joints, enhance the activity of local osteoblasts in a joint, and/or reduce the activity of osteoclasts, promote cartilage regeneration and the bone remodeling of subchondral bone, and effectively relieve pain and other symptoms; thereby developing a new way for treating joint injury diseases including osteoarthritis.

Particularly, the present invention relates to:
1. A method for treating osteoarthritis, which includes administering an effective amount of plasminogen to a subject.
2. The method according to item 1, the plasminogen increases the amount of articular cartilage, and/or promotes the repair of articular cartilage injury.
3. The method according to item 1 or 2, the plasminogen improves the inflammation condition of joint synovium.
4. The method according to any one of items 1-3, the plasminogen promotes the bone remodeling of subchondral bone for joints.
5. The method according to any one of items 1-4, wherein the plasminogen improves the inflammation condition and pain of joint, and/or improves joint function.
6. The method according to any one of items 1-5, wherein the plasminogen reduces joint swelling and pain.
7. A method for promoting the regeneration of articular cartilage in an osteoarthritis subject, which includes administering an effective amount of plasminogen to the subject.
8. A method for promoting the repair of joint injury in a subject, which includes administering an effective amount of plasminogen to the subject.
9. The method according to item 8, wherein the plasminogen promotes the regeneration of articular cartilage and/or the bone remodeling of subchondral bone.
10. The method according to item 8 or 9, wherein the subject is an osteoarthritis subject.
11. The method according to any one of items 8-10, wherein the plasminogen improves the inflammation condition of joint tissue, and/or reduces joint pain.
12. The method according to any one of items 1-11, wherein the plasminogen has at least 75%, 80%, 85%, 90%, 95%, 96%, 97%, 98%, or 99% sequence identity with SEQ ID NO: 2, and still has plasminogen activity.
13. The method according to any one of items 1-11, wherein the plasminogen is a protein comprising a plasminogen active fragment and still having plasminogen activity.
14. The method according to any one of items 1-11, wherein the plasminogen is selected from Glu-plasminogen. Lys-plasminogen, small plasminogen, microplasminogen, delta-plasminogen, or their variants retaining plasminogen activity.

15. The method according to any one of items 1-11, wherein the plasminogen is natural or synthetic human plasminogen, or a variant or fragment thereof still retaining plasminogen activity.
16. The method according to any one of items 1-11, wherein the plasminogen is an ortholog of human plasminogen from a primate or rodent, or a variant or fragment thereof retaining plasminogen activity.
17. The method according to any one of items 1-11, wherein the amino acid sequence of the plasminogen is represented by SEQ ID NO: 2, 6, 8, 10, or 12.
18. The method according to any one of items 1-11, wherein the plasminogen is human native plasminogen.
19. The method according to any one of items 1-18, wherein the subject is a human.
20. The method according to any one of items 1-19, wherein the subject is deficient in or lacks plasminogen.
21. The method according to any one of items 1-20, wherein the plasminogen is used in combination with one or more medicaments or methods for treating joint injury, or one or more medicaments or methods for treating osteoarthritis.
22. A plasminogen for use in the method according to any of items 1-21.
23. A pharmaceutical composition, comprising a pharmaceutically acceptable carrier, and a plasminogen for use in the method according to any one of items 1-21.
24. A prophylactic or therapeutic kit, comprising: (i) a plasminogen for use in the method according to any of items 1-21, and (ii) component/means for delivering the plasminogen to the subject.
25. The kit according to item 24, wherein the component is a syringe or a vial.
26. The kit according to item 24 or 25, further comprising a label or an instruction manual indicating that the plasminogen is administered to the subject to perform the method according to any one of items 1-21.
27. A product comprising: a container with label; and comprising (i) a plasminogen for use in the method according to any one of items 1-21, or a pharmaceutical composition comprising the plasminogen, wherein the label indicates that the plasminogen or composition is administered to the subject to perform the method according to any one of items 1-21.
28. The kit according to any one of items 24-26 or the product according to item 27, further comprising one or more components or containers which contains one or more other medicaments or supplies for treating joint injury, or one or more other medicaments or supplies for treating osteoarthritis.
29. The kit according to any one of items 24-26 or the product according to item 27, further includes medicaments for treating other diseases concomitant with osteoarthritis.
30. An agent containing plasminogen for treating osteoarthritis.
31. An agent containing plasminogen for treating joint injury.
32. A pharmaceutical composition, kit, and product containing plasminogen for treating osteoarthritis.
33. A pharmaceutical composition, kit, and product containing plasminogen for treating joint injury.
34. Use of plasminogen in the preparation of a medicament, product, or kit for treating osteoarthritis.
35. The use according to item 34, the plasminogen increases the amount of articular cartilage, and/or promotes the repair of articular cartilage injury.
36. The use according to item 34 or 35, the plasminogen improves the inflammation condition of joint synovium.
37. The use according to any one of items 34-36, the plasminogen promotes the bone remodeling of subchondral bone for joints.
38. The use according to any one of items 34-37, wherein the plasminogen improves the inflammatory condition and pain of joints, and/or improves joint function.
39. The use according to any one of items 34-38, wherein the plasminogen reduces joint swelling and pain.
40. Use of plasminogen in the preparation of a medicament for promoting the regeneration of articular cartilage in an osteoarthritis subject.
41. Use of plasminogen in the preparation of a medicament for promoting the repair of joint injury in a subject.
42. The use according to item 41, the plasminogen promotes the regeneration of articular cartilage and/or the bone remodeling of subchondral bone.
43. The use according to item 41 or 42, wherein the subject is an osteoarthritis subject.
44. The use according to any one of items 41-43, wherein the plasminogen improves the inflammation condition of joint tissues, and/or reduces joint pain.
45. The method according to any one of items 34-44, wherein the plasminogen has at least 75%, 80%, 85%, 90%, 95%, 96%, 97%, 98%, or 99% of sequence identity with SEQ ID NO: 2, 6, 8, 10, or 12, and still have plasminogen activity.
46. The use according to any one of items 34-44, wherein the plasminogen is a protein containing a plasminogen active fragment and still having plasminogen activity.
47. The use according to any one of items 34-44, the plasminogen is selected from Glu-plasminogen Lys-plasminogen, small plasminogen, microplasminogen, and delta-plasminogen, or their variants retaining plasminogen activity.
48. The use according to any one of items 34-44, wherein the plasminogen is natural or synthetic human plasminogen, or a variant or fragment thereof retaining plasminogen activity.
49. The use according to any one of items 34-44, wherein the plasminogen is an ortholog of human plasminogen from a primate or rodent, or a variant or fragment thereof retaining plasminogen activity.
50. The use according to any one of items 34-44, wherein the amino acid sequence of the plasminogen is represented by SEQ ID NO: 2, 6, 8, 10, or 12.
51. The use according to any one of items 34-44, wherein the plasminogen is human native plasminogen.
52. The use according to any one of items 34-51, wherein the subject is a human.
53. The use according to any one of items 34-52, wherein the plasminogen is used in combination with one or more medicaments or methods for treating joint injury, or one or more medicaments or methods for treating osteoarthritis.

DETAILED DESCRIPTION OF THE INVENTION

Definition of Terms, and Description of Technical Solutions

The "joint" is the connecting tissue between the bones. There is a cavity in the connecting tissue, which enables joint to do activities at different degrees. The main structures of a joint are joint capsule, articular cavity, articular cartilage, synovia, as well as ligaments, muscles and tendons around the joint, synovial folds, bursa mucosa, meniscus, subchondral bone, etc. The joint capsule is a connective tissue membrane sac that surrounds the two opposite bone ends of the joint. It consists of the inner and outer layers: the outer layer is a fibrous layer composed of dense connective tissue, and it is thick and tough, and mainly plays a role in maintaining the firmness and stability of the joint: the inner layer is a thin and soft synovial layer composed of loose connective tissue rich in blood vessels, and it covers the inner surface of the fiber layer to form a sac surrounding the synovial cavity. The articular cavity is a tissue cavity formed by the joint capsule and the joint surface. Under normal circumstances, there will be a little viscous liquid (i.e., synovia) in the articular cavity, which has the effect of lubricating and nourishing the joint. Articular cartilage refers to the thin layer of cartilage covering the surface of the joint, and it covers the joint surface and has good elasticity, thereby reducing friction, cushioning shock and impact. Synovia is synovial fluid, and is secreted by the synovial membrane. Normal synovia is clear and viscous. When the joint is inflamed, the amount of synovia increases significantly, and the pressure in the articular cavity increases, thereby resulting in local swelling and pain.

Some embodiments of the present invention relate to a method for treating joint injury by plasminogen and a method for promoting the repair of joint injury in a subject with joint injury, comprising: administering an effective amount of plasminogen to the subject. In some embodiments, the joint injury includes joint injury caused by inflammation condition, degenerative disease, metabolic disorder, or trauma. In some embodiments, the plasminogen treats joint injury or promotes the repair of joint injury by promoting the regeneration of articular cartilage and/or the bone remodeling of subchondral bone. In some embodiments, the plasminogen improves inflammation condition and/or reduces joint pain in joint tissue of a subject with joint injury. In some embodiments, the inflammation condition of the joint tissue includes inflammation condition of the joint synovium. In some embodiments, the plasminogen reduces joint swelling and pain in a joint injury subject.

In some embodiments, the present invention relates to a method for promoting the regeneration of articular cartilage, comprising: administering an effective amount of plasminogen to a subject. In some embodiments, the present invention relates to promoting the repair of joint injury and treating joint injury diseases via the enhancement of cartilage regeneration by plasminogen.

In some above-mentioned embodiments for treating joint injury and promoting the repair of joint injury by plasminogen, the joint injury is caused by osteoarthritis.

In some above-mentioned embodiments for treating joint injury and promoting the repair of joint injury by plasminogen, the plasminogen promotes the regeneration of articular cartilage and/or the bone remodeling of subchondral bone, so that the joint injury is repaired, thereby the process of development of joint injury into osteoarthritis is cut off. Therefore, the present invention also relates to a method for preventing osteoarthritis by plasminogen, which comprises administering an effective amount of plasminogen to a subject with joint injury.

In all the above methods for treating joint injury, promoting the repair of joint injury, promoting cartilage regeneration, and preventing joint injury from developing into osteoarthritis by plasminogen, the plasminogen may be administered alone or in combination with one or more other medicaments or methods. The co-administration includes administration of plasminogen before, at the same time of, or after the administration of one or more other medicaments or methods.

"Osteoarthritis (OA)" is a degenerative disease, which is caused by degeneration and injury of articular cartilage, and reactive hyperplasia of joint margins and subchondral cartilage due to many factors such as aging, obesity, strain, trauma, congenital abnormalities of joints, and joint deformities; and it is also known as osteoarthropathy, degenerative arthritis, senile arthritis, etc. The clinical manifestations are slowly developing joint pain, tenderness, stiffness, joint swelling, restricted mobility, and joint deformities, etc.

Osteoarthritis is a degenerative disease of bone joints, which occurs in weight-bearing joints and joints with a lot of activity, such as cervical vertebrae, lumbar vertebrae, knee joints, and hip joints. Excessive weight-bearing or overuse of these joints can promote the occurrence of degenerative changes. The clinical manifestations are slowly developing joint pain, tenderness, stiffness, joint swelling, restricted mobility, and joint deformities. Imaging changes include abnormal changes in articular cartilage and subchondral bone, joint space narrowing (this indicates that articular cartilage has begun to thin), calcification of bone, sharpening of the edge of joint, osteophyte formation, and/or the formation of subchondral bone cyst. The "osteoarthritis" according to the present invention covers osteoarthritis occurring in various parts of the body, including the osteoarthritis or related degenerative lesions in the cervical vertebrae, lumbar vertebrae, knee joints, and hip joints.

Some embodiments of the present invention relate to a method for treating osteoarthritis by plasminogen, which comprises administering an effective amount of plasminogen to a subject. In some embodiments, the plasminogen promotes the regeneration of articular cartilage and/or the bone remodeling of subchondral bone. In some embodiments, the plasminogen improves the inflammation condition of joint tissue, and/or reduces joint swelling and/or pain. In some embodiments, the plasminogen improves inflammation condition of the joint synovium, and/or reduces joint swelling and/or pain. In some embodiments, the osteoarthritis is osteoarthritis in the cervical vertebrae, lumbar vertebrae, knee joints and hip joints, or related degenerative diseases.

In the above embodiments for treating osteoarthritis by plasminogen, the "treatment" includes reducing, relieving, ameliorating or eliminating one or more of the following symptoms or signs: joint pain, tenderness, stiffness, joint swelling, joint function disorders or limitations, abnormal changes in articular cartilage or subchondral bone, stenosis of joint space, calcification of bone, sharpening of joint margins, osteophytes, subchondral bone cyst. In the embodiment for treating osteoarthritis by plasminogen, the osteoarthritis includes osteoarthritis of the cervical vertebrae, lumbar vertebrae, knee joints and hip joints, and related degenerative diseases.

"Bone remodeling" is also called "bone metabolism", and refers to the removal of mature bone tissue from the bone (a process called bone resorption) and the formation of new bone tissue (a process called ossification or new bone formation). These processes also control the reshaping or replacement of bones after fractures and other injuries, as well as micro-damages that occur during normal activities. Remodeling also responds to the functional requirements of mechanical loads. The structure of the bone and the adequate supply of calcium, require close cooperation between the two types of cells, i.e., osteoblasts (secreting new bone) and osteoclasts (destroying the bone), and other cell groups (such as immune cells, etc.) present in the bone remodeling site, and rely on complex signal transduction pathway and control mechanism, so as to achieve an appropriate growth and differentiation rate.

In some embodiments, the present invention relates to promoting the regeneration of articular cartilage and/or the bone remodeling of subchondral bone by plasminogen. In some embodiments, the present invention relates to promoting (enhancing) the activity of osteoblasts and/or reducing the activity of osteoclasts at the site of osteoarthritis in an osteoarthritis subject by plasminogen.

In some embodiments, the present invention relates to a method for promoting the repair of joint injury in a subject by plasminogen, comprising: administering to the subject an effective amount of plasminogen. In some embodiments, the joint injury includes a joint injury caused by inflammation condition, degenerative disease, metabolic disorder, or trauma. In some embodiments, the plasminogen treats joint injury or promotes the repair of joint injury by promoting the regeneration of articular cartilage and/or the bone remodeling of subchondral bone. In some embodiments, the plasminogen promotes (enhances) the activity of osteoblasts and/or reduces the activity of osteoclasts at the joint injury site of the subject with joint injury. In some embodiments, the joint injury is a joint injury caused by osteoarthritis. In some embodiments, the joint injury is a joint injury caused by inflammation, metabolic disorders, or trauma.

"Improving" inflammation (condition) of joint synovium, "improving" inflammation (condition) of joint, "improving" inflammation (condition) of joint tissue, or "improving" inflammation of joint tissue, means inflammation or inflammatory condition is improved after the treatment of administering plasminogen, and the inflammatory response is eventually relieved and resolved.

In all the above embodiments for treating osteoarthritis by plasminogen, the plasminogen can be administered alone or in combination with one or more other medicaments or methods. The co-administration includes administration of plasminogen before, at the same time of, or after the administration of one or more other medicaments or methods.

Plasmin is a key component of the plasminogen activation system (PA system). It is a broad-spectrum protease capable of hydrolyzing several components of the extracellular matrix (ECM), including fibrin, gelatin, fibronectin, laminin, and proteoglycan [5]. In addition, plasmin can activate some precursors of metalloproteinase (pro-MMPs) to form active metalloproteases (MMPs). Therefore, plasmin is considered to be an important upstream regulator of extracellular proteolysis [6,7]. Plasmin is formed by proteolysis of plasminogen through two physiological PAs: tissue-type plasminogen activator (tPA) or urokinase-type plasminogen activator (uPA). Due to the relatively high levels of plasminogen in plasma and other body fluids, it is typically believed that the regulation of the PA system is mainly achieved through the synthesis and activity levels of PAs. The synthesis of the components of PA system is strictly regulated by different factors, such as hormones, growth factors and cytokines. In addition, there are specific physiological inhibitors of plasmin and PAs. The main inhibitor of plasmin is α2-antiplasmin (α2-antiplasmin). The activity of PAs is regulated by both the plasminogen activator inhibitor-1 (PAI-1) of uPA and tPA and the plasminogen activator inhibitor-2 (PAI-2) which mainly inhibits uPA. The surface of certain cells has uPA-specific cell surface receptors (uPAR) with direct hydrolytic activity [8,9].

Plasminogen is a single-chain glycoprotein consisting of 791 amino acids with a molecular weight of approximately 92 kDa [10,11]. Plasminogen is mainly synthesized in the liver, and is abundant in extracellular fluid. Plasminogen content in plasma is about 2 μM. Therefore, plasminogen is a huge potential source of proteolytic activity in tissues and body fluids [12,13]. There are two molecular forms of plasminogen: glutamate-plasminogen (Glu-plasminogen) and lysine-plasminogen (Lys-plasminogen). The naturally secreted and uncleaved form of plasminogen has an amino-terminal (N-terminal) glutamic acid, and is therefore called glutamate-plasminogen. However, in the presence of plasmin, glutamate-plasminogen is hydrolyzed to lysine-plasminogen at Lys76-Lys77. Compared with glutamate-plasminogen, lysine-plasminogen has a higher affinity for fibrin, and can be activated by PAs at a higher rate. The Arg560-Val561 peptide bond of these two forms of plasminogen can be cleaved by uPA or tPA, resulting in the formation of a disulfide-linked double-chain protease plasmin [14]. The amino-terminal portion of plasminogen contains five homologous triple-loops, so-called kringles, and the carboxy-terminal portion contains a protease domain. Some kringles contain lysine binding sites that mediate the specific interaction of plasminogen with fibrin and its inhibitor α2-AP. The latest discovered plasminogen is a 38 kDa fragment including kringles 1-4, and it is an effective inhibitor of angiogenesis. This fragment is named angiostatin, and can be produced by the hydrolysis of plasminogen by several proteases.

The main substrate of plasmin is fibrin, and the dissolution of fibrin is the key to preventing pathological thrombosis [15]. Plasmin also has substrate specificity for several components of ECM including laminin, fibronectin, proteoglycan, and gelatin, and this indicates that plasmin also plays an important role in ECM reconstruction [11,16, 17]. Indirectly, plasmin can also degrade other components of ECM by converting certain protease precursors into active proteases, including MMP-1, MMP-2, MMP-3 and MMP-9. Therefore, it has been suggested that plasmin may be an important upstream regulator of extracellular proteolysis [18]. In addition, plasmin has the ability to activate certain potential forms of growth factors [19-21]. In vitro plasmin can also hydrolyze components of the complement system, and release chemotactic complement fragments.

"Plasmin" is a very important enzyme that exists in the blood and is capable of hydrolyzing fibrin clots into fibrin degradation products and D-dimers.

"Plasminogen" is the zymogen form of plasmin, and it is a glycoprotein composed of 810 amino acids calculated based on the amino acid sequence (SEQ ID NO: 4) of the native human plasminogen containing a signal peptide according to the sequence in the swiss prot, having a molecular weight of about 90 kD, being synthesized mainly in the liver and being capable of circulating in the blood; and the cDNA sequence encoding this amino acid sequence is as shown in SEQ ID NO: 3. Full-length plasminogen contains seven domains: a C-terminal serine protease domain, an N-terminal Pan Apple (PAp) domain and five Kringle domains (Kringles 1-5). Referring to the sequence in the swiss prot, the signal peptide comprises residues Met1-Gly19. PAp comprises residues Glu20-Val98, Kringle 1 comprises residues Cys103-Cys181, Kringle 2 comprises residues Glu184-Cys262, Kringle 3 comprises residues Cys275-Cys352, Kringle 4 comprises residues Cys377-Cys454, and Kringle 5 comprises residues Cys481-Cys560. According to the NCBI data, the serine protease domain comprises residues Val581-Arg804.

Glu-plasminogen is a native full-length plasminogen and is composed of 791 amino acids (without a signal peptide of 19 amino acids): the cDNA sequence encoding this sequence is as shown in SEQ ID NO: 1; and the amino acid sequence is as shown in SEQ ID NO: 2. In vivo, Lys-plasminogen, which is formed by hydrolysis of amino acids at positions 76-77 of Glu-plasminogen, is also present, as shown in SEQ ID No.6; and the cDNA sequence encoding this amino acid sequence is as shown in SEQ ID No.5. δ-plasminogen is a fragment of full-length plasminogen that lacks the structure of Kringle 2-Kringle 5 and contains only Kringle 1 and the serine protease domain [22,23]. The amino acid sequence (SEQ ID No.8) of δ-plasminogen has been reported in the literature [23], and the cDNA sequence encoding this amino acid sequence is as shown in SEQ ID No.7. Mini-plasminogen is composed of Kringle 5 and the serine protease domain, and has been reported in the literature to comprise residues Val443-Asn791 (with the Glu residue of the Glu-plasminogen sequence that does not contain a signal peptide as the starting amino acid) [24]; the amino acid sequence is as shown in SEQ ID NO: 10: and the cDNA sequence encoding this amino acid sequence is as shown in SEQ ID NO: 9. In addition, micro-plasminogen comprises only the serine protease domain, the amino acid sequence of which has been reported in the literature to comprise residues Ala543-Asn791 (with the Glu residue of the Glu-plasminogen sequence that does not contain a signal peptide as the starting amino acid) [25], and the sequence of which has been also reported in patent literature CN102154253A to comprise residues Lys531-Asn791 (with the Glu residue of the Glu-plasminogen sequence that does not contain a signal peptide as the starting amino acid) (the sequence in this patent application refers to the patent literature CN102154253A); the amino acid sequence is as shown in SEQ ID NO: 12 and the cDNA sequence encoding this amino acid sequence is as shown in SEQ ID NO: 11.

In the present invention, "plasmin" is used interchangeably with "fibrinolysin" and "fibrinolytic enzyme", and the terms have the same meaning; and "plasminogen" is used interchangeably with "profibrinolysin" and "fibrinolytic zymogen", and the terms have the same meaning.

In the present application, the "deficiency" of plasminogen or its activity means that the content of plasminogen in a subject is lower than that of a normal person, i.e., being low enough to affect the normal physiological function of the subject; the "lack" of plasminogen or its activity means that the content of plasminogen in a subject is significantly lower than that of a normal person, and even the activity or expression is extremely low so that the normal physiological function can only be maintained by providing external source of plasminogen.

Those skilled in the art can understand that all the technical solutions of the plasminogen of the present invention are suitable for plasmin. Therefore, the technical solutions described in the present invention cover plasminogen and plasmin.

In the course of circulation, plasminogen is in a closed, inactive conformation, but when bound to thrombi or cell surfaces, it is converted into an active plasmin in an open conformation under the mediation of a plasminogen activator (PA). The active plasmin can further hydrolyze the fibrin clots to fibrin degradation products and D-dimers, thereby dissolving the thrombi. The PAp domain of plasminogen comprises an important determinant that maintains plasminogen in an inactive, closed conformation, and the KR domain is capable of binding to lysine residues present on receptors and substrates. A variety of enzymes that can serve as plasminogen activators are known, including: tissue plasminogen activator (tPA), urokinase plasminogen activator (uPA), kallikrein, coagulation factor XII (Hagmann factor), and the like.

"Plasminogen active fragment" refers to an active fragment in the plasminogen protein that is capable of binding to a target sequence in a substrate and exerting the proteolytic function. The technical solutions of the present invention involving plasminogen comprise such a technical solution in which plasminogen is replaced with a plasminogen active fragment. The plasminogen active fragment of the present invention is a protein comprising a serine protease domain of plasminogen. Preferably, the plasminogen active fragment of the present invention comprises SEQ ID No.14, or an amino acid sequence having an amino acid sequence identity of at least 80%, 90%, 95%, 96%, 97%, 98% or 99% with SEQ ID No.14. Therefore, plasminogen of the present invention comprises a protein containing the plasminogen active fragment and still having the plasminogen activity.

At present, methods for determining plasminogen and its activity in blood include: detection of tissue plasminogen activator activity (t-PAA), detection of tissue plasminogen activator antigen (t-PAAg) in plasma, detection of tissue plasminogen activity (pIgA) in plasma, detection of tissue plasminogen antigen (pIgAg) in plasma, detection of activity of the inhibitor of tissue plasminogen activators in plasma, detection of inhibitor antigens of tissue plasminogen activators in plasma and detection of plasmin-anti-plasmin (PAP) complex in plasma. The most commonly used detection method is the chromogenic substrate assay: streptokinase (SK) and a chromogenic substrate are added to a test plasma, the plasminogen in the test plasma is converted into plasmin by the action of SK, plasmin acts on the chromogenic substrate, and then it is determined that the increase in absorbance is directly proportional to plasminogen activity using a spectrophotometer. In addition, plasminogen activity in blood can also be determined by immunochemistry, gel electrophoresis, immunonephelometry, radioimmuno-diffusion and the like.

"Orthologues or orthologs" refer to homologs between different species, including both protein homologs and DNA homologs, and are also known as orthologs homologs and vertical homologs. The term specifically refers to proteins or genes that have evolved from the same ancestral gene in different species. The plasminogen of the present invention includes human native plasminogen, and also includes orthologues or orthologs of plasminogens derived from different species and having plasminogen activity.

"Conservative substitution variant" refers to one in which a given amino acid residue is changed without altering the overall conformation and function of the protein or enzyme, including, but not limited to, replacing an amino acid in the amino acid sequence of the parent protein by an amino acid with similar properties (such as acidity, alkalinity, hydrophobicity, etc.). Amino acids with similar properties are well known. For example, arginine, histidine and lysine are hydrophilic basic amino acids and are interchangeable. Similarly, isoleucine is a hydrophobic amino acid that can be replaced by leucine, methionine or valine. Therefore, the similarity of two proteins or amino acid sequences with similar functions may be different. For example, the similarity (identity) is 70%-99% based on the MEGALIGN algorithm. "Conservation substitution variant" also includes a polypeptide or enzyme having amino acid identity of 60% or more, preferably 75% or more, more preferably 85% or more, even more preferably 90% or more as determined by the BLAST or FASTA algorithm, and having the same or substantially similar properties or functions as the native or parent protein or enzyme. "Isolated" plasminogen refers to the plasminogen protein that is isolated and/or recovered from its natural environment. In some embodiments, the plasminogen will be purified (1) to a purity of greater than 90%, greater than 95% or greater than 98% (by weight), as determined by the Lowry method, such as more than 99% (by weight); (2) to a degree sufficiently to obtain at least 15 residues of the N-terminal or internal amino acid sequence using a spinning cup sequenator; or (3) to homogeneity, which is determined by sodium dodecyl sulfate-polyacrylamide gel electrophoresis (SDS-PAGE) under reducing or non-reducing conditions using Coomassie blue or silver staining. Isolated plasminogen also includes plasminogen prepared from recombinant cells by bioengineering techniques and separated by at least one purification step.

The terms "polypeptide", "peptide" and "protein" are used interchangeably herein and refer to polymeric forms of amino acids of any length, which may include genetically encoded and non-genetically encoded amino acids, chemically or biochemically modified or derivative amino acids, and polypeptides having modified peptide backbones. The term includes fusion proteins, including, but not limited to, fusion proteins having heterologous amino acid sequences, fusions having heterologous and homologous leader sequences (with or without N-terminal methionine residues); and the like.

The "percent amino acid sequence identity (%)" with respect to the reference polypeptide sequence is defined as the percentage of amino acid residues in the candidate sequence identical to the amino acid residues in the reference polypeptide sequence when a gap is introduced as necessary to achieve maximal percent sequence identity and no conservative substitutions are considered as part of sequence identity. The comparison for purposes of determining percent amino acid sequence identity can be achieved in a variety of ways within the technical scope of the art, for example using publicly available computer softwares, such as BLAST, BLAST-2, ALIGN or Megalign (DNASTAR) software. Those skilled in the art can determine appropriate parameters for aligning sequences, including any algorithm needed to achieve the maximum comparison over the full length of the sequences being compared. However, for purposes of the present invention, the percent amino acid sequence identity value is generated using the sequence comparison computer program ALIGN-2.

In the case of comparing amino acid sequences using ALIGN-2, the % amino acid sequence identity of a given amino acid sequence A relative to a given amino acid sequence B (or may be expressed as a given amino acid sequence A having or containing a certain % amino acid sequence identity relative to, with or for a given amino acid sequence B) is calculated as follows:

fraction $X/Y \times 100$ wherein X is the number of identically matched amino acid residues scored by the sequence alignment program ALIGN-2 in the alignment of A and B using the program, and wherein Y is the total number of amino acid residues in B. It will be appreciated that where the length of amino acid sequence A is not equal to the length of amino acid sequence B, the % amino acid sequence identity of A relative to B will not be equal to the % amino acid sequence identity of B relative to A. Unless specifically stated otherwise, all the % amino acid sequence identity values used herein are obtained using the ALIGN-2 computer program as described in the previous paragraph.

As used herein, the terms "treatment" and "treating" refer to obtaining a desired pharmacological and/or physiologic effect. The effect may be complete or partial prevention of a disease or its symptoms and/or partial or complete cure of the disease and/or its symptoms, and includes: (a) prevention of the disease from developing in a subject that may have a predisposition to the disease but has not been diagnosed as having the disease; (b) suppression of the disease, i.e., blocking its formation; and (c) alleviation of the disease and/or its symptoms, i.e., eliminating the disease and/or its symptoms.

The terms "individual", "subject" and "patient" are used interchangeably herein and refer to mammals, including, but not limited to, murine (rats and mice), non-human primates, humans, dogs, cats, hoofed animals (e.g., horses, cattle, sheep, pigs, goats) and so on.

"Therapeutically effective amount" or "effective amount" refers to an amount of plasminogen sufficient to achieve the prevention and/or treatment of a disease when administered to a mammal or another subject to treat the disease. The "therapeutically effective amount" will vary depending on the plasminogen used, the severity of the disease and/or its symptoms, as well as the age, body weight of the subject to be treated, and the like.

Preparation of the Plasminogen of the Present Invention

Plasminogen can be isolated and purified from nature for further therapeutic uses, and can also be synthesized by standard chemical peptide synthesis techniques. When chemically synthesized, a polypeptide can be subjected to liquid or solid phase synthesis. Solid phase polypeptide synthesis (SPPS) is a method suitable for chemical synthesis of plasminogen, in which the C-terminal amino acid of a sequence is attached to an insoluble support, followed by the sequential addition of the remaining amino acids in the sequence. Various forms of SPPS, such as Fmoc and Boc, can be used to synthesize plasminogen. Techniques for solid phase synthesis are described in Barany and Solid-Phase Peptide Synthesis: pp. 3-284 in The Peptides: Analysis, Synthesis, Biology. Vol. 2: Special Methods in Peptide Synthesis, Part A., Merrifield et al. J. Am. Chem. Soc., 85: 2149-2156 (1963): Stewart et al. Solid Phase Peptide Synthesis, 2nd ed. Pierce Chem. Co., Rockford, Ill. (1984): and Ganesan A. 2006 Mini Rev. Med Chem. 6:3-10 and Camarero J A et al. 2005 Protein Pept Lett. 12:723-8. Briefly, small insoluble porous beads are treated with a functional unit on which a peptide chain is constructed. After repeated cycles of coupling/deprotection, the attached solid phase free N-terminal amine is coupled to a single N-protected amino acid unit. This unit is then deprotected to expose a new N-terminal amine that can be attached to another amino acid. The peptide remains immobilized on the solid phase before it is cut off.

Standard recombinant methods can be used to produce the plasminogen of the present invention. For example, a nucleic acid encoding plasminogen is inserted into an expression vector, so that it is operably linked to a regulatory sequence in the expression vector. Expression regulatory sequence includes, but is not limited to, promoters (e.g., naturally associated or heterologous promoters), signal sequences, enhancer elements and transcription termination sequences. Expression regulation can be a eukaryotic promoter system in a vector that is capable of transforming or transfecting eukaryotic host cells (e.g., COS or CHO cells). Once the vector is incorporated into a suitable host, the host is maintained under conditions suitable for high-level expression of the nucleotide sequence and collection and purification of plasminogen.

A suitable expression vector is usually replicated in a host organism as an episome or as an integral part of the host chromosomal DNA. In general, an expression vector contains a selective marker (e.g., ampicillin resistance, hygromycin resistance, tetracycline resistance, kanamycin resistance or neomycin resistance) to facilitate detection of those exogenous cells transformed with a desired DNA sequence.

*Escherichia coli* is an example of prokaryotic host cells that can be used to clone a polynucleotide encoding the subject antibody. Other microbial hosts suitable for use include *Bacillus*, for example, *Bacillus subtilis* and other species of enterobacteriaceae (such as genus *Salmonella* and genus *Serratia*), and various genus *Pseudomonas*. In these prokaryotic hosts, expression vectors can also be generated which will typically contain an expression control sequence (e.g., origin of replication) that is compatible with the host cell. In addition, there will be many well-known promoters, such as the lactose promoter system, the tryptophan (trp) promoter system, the beta-lactamase promoter system or the promoter system from phage A. Optionally in the case of manipulation of a gene sequence, a promoter will usually control expression, and has a ribosome binding site sequence and the like to initiate and complete transcription and translation.

Other microorganisms, such as yeast, can also be used for expression. *Saccharomyces* (e.g., *S. cerevisiae*) and *Pichia* are examples of suitable yeast host cells, in which a suitable vector has an expression control sequence (e.g., promoter), an origin of replication, a termination sequence and the like, as required. A typical promoter comprises 3-phosphoglycerate kinase and other glycolytic enzymes. Inducible yeast is initiated by promoters specifically including those derived from alcohol dehydrogenase, isocytochrome C. and enzymes responsible for maltose and galactose utilization.

In addition to microorganisms, mammalian cells (e.g., mammalian cells cultured in cell culture material in vitro) may also be used to express and produce the anti-Tau antibody (e.g., a polynucleotide encoding the subject anti-Tau antibody) of the present invention. See Winnacker, From Genes to Clones, VCH Publishers, N.Y., N.Y. (1987). Suitable mammalian host cells include CHO cell lines, various Cos cell lines, HeLa cells, myeloma cell lines and transformed B cells or hybridomas. Expression vectors for these cells may comprise an expression control sequence, such as an origin of replication, promoter and enhancer (Queen et al. Immunol. Rev. 89:49 (1986)), as well as necessary information processing sites, such as a ribosome binding site, RNA splice site, polyadenylation site and transcription terminator sequence. Examples of suitable expression control sequences are promoters derived from immunoglobulin gene, SV40, adenovirus, bovine papilloma virus, cytomegalovirus and the like. See Co et al. J. Immunol. 148:1149 (1992).

Once synthesized (chemically or recombinantly), the plasminogen of the present invention can be purified according to standard procedures in the art, including ammonium sulfate precipitation, affinity column, column chromatography, high performance liquid chromatography (HPLC), gel electrophoresis and the like. The plasminogen is substantially pure, e.g., at least about 80% to 85% pure, at least about 85% to 90% pure, at least about 90% to 95% pure, or 98% to 99% pure or purer, for example free of contaminants such as cell debris, macromolecules other than the subject antibody and the like.

Pharmaceutical Formulations

A therapeutic formulation can be prepared by mixing plasminogen of a desired purity with an optional pharmaceutical carrier, excipient or stabilizer (Remington's Pharmaceutical Sciences, 16th edition. Osol, A. ed. (1980)) to form a lyophilized preparation or an aqueous solution. Acceptable carriers, excipients and stabilizers are non-toxic to the recipient at the dosages and concentrations employed, and include buffers, such as phosphates, citrates and other organic acids antioxidants, including ascorbic acid and methionine; preservatives (e.g., octadecyl dimethyl benzyl ammonium chloride hexane chloride diamine; benzalkonium chloride and benzethonium chloride: phenol, butanol or benzyl alcohol alkyl p-hydroxybenzoates, such as methyl or propyl p-hydroxybenzoate; catechol; resorcinol; cyclohexanol; 3-pentanol; and m-cresol); low molecular weight polypeptides (less than about 10 residues): proteins, such as serum albumin. gelatin or immunoglobulins; hydrophilic polymers, such as polyvinylpyrrolidone; amino acids, such as glycine, glutamine, asparagine, histidine, arginine or lysine; monosaccharides, disaccharides and other carbohydrates, including glucose, mannose or dextrins; chelating agents, such as EDTA; sugars, such as sucrose, mannitol, fucose or sorbitol; salt-forming counter ions, such as sodium metal complexes (e.g., zinc-protein complexes); and/or non-ionic surfactants, e.g., TWEEN™, PLURONICS™, or polyethylene glycol (PEG). Preferable formulation of lyophilized anti-VEGF antibody is described in WO 97/04801, which is incorporated herein by reference.

The formulations of the invention may also comprise one or more active compounds required for the particular disorder to be treated, preferably those that are complementary in activity and have no side effects with one another, for instance, drugs for treating hypertension, arrhythmia, and diabetes, etc.

The plasminogen of the present invention may be encapsulated in microcapsules prepared by techniques such as coacervation or interfacial polymerization, for example, it may be incorporated in a colloid drug delivery system (e.g., liposomes, albumin microspheres, microemulsions, nanoparticles and nanocapsules), or incorporated in hydroxymethyl cellulose or gel-microcapsules and poly-(methyl methacrylate) microcapsules in macroemulsions. These techniques are disclosed in Remington's Pharmaceutical Sciences, 16th edition, Osol, A. Ed. (1980).

The plasminogen of the present invention for in vivo administration must be sterile. This can be easily achieved by filtration through a sterile filtration membrane before or after lyophilization and reconstitution.

The plasminogen of the present invention can be prepared into a sustained-release preparation. Suitable examples of sustained-release preparations include solid hydrophobic polymer semi-permeable matrices having a shape and containing glycoproteins, such as films or microcapsules. Examples of sustained-release matrices include polyesters, hydrogels (e.g., poly(2-hydroxyethyl-methacrylate)) (Langer et al. J. Biomed. Mater. Res., 15: 167-277 (1981) and Langer, Chem. Tech., 12:98-105 (1982)), or poly(vinyl alcohol), polylactides (U.S. Pat. No. 3,773,919, and EP 58,481), copolymer of L-glutamic acid and y ethyl-L-glutamic acid (Sidman et al. Biopolymers 22:547(1983)), non-degradable ethylene-vinyl acetate (Langer et al. supra), or degradable lactic acid-glycolic acid copolymers such as Lupron Depot™ (injectable microspheres composed of lactic acid-glycolic acid copolymer and leuprolide acetate), and poly D-(−)-3-hydroxybutyric acid. Polymers, such as ethylene-vinyl acetate and lactic acid-glycolic acid, are able to persistently release molecules for 100 days or longer, while some hydrogels release proteins for a shorter period of time. A rational strategy for protein stabilization can be designed based on relevant mechanisms. For example, if the aggregation mechanism is discovered to be formation of an intermolecular S—S bond through thio-disulfide interchange, stability is achieved by modifying sulhydryl residues, lyophilizing from acidic solutions, controlling moisture content, using appropriate additives, and developing specific polymer matrix compositions.

Administration and Dosage

The pharmaceutical composition of the present invention can be administered in different ways, for example by intravenous, intraperitoneal, subcutaneous, intracranial, intrathecal, intraarterial (e.g., via carotid), intramuscular administration.

Preparations for parenteral administration include sterile aqueous or non-aqueous solutions, suspensions and emulsions. Examples of non-aqueous solvents are propylene glycol, polyethylene glycol, vegetable oils such as olive oil, and injectable organic esters such as ethyl oleate. Aqueous carriers include water, and alcoholic/aqueous solutions, emulsions or suspensions, including saline and buffered media. Parenteral vehicles include sodium chloride solution, Ringer's dextrose, dextrose and sodium chloride, or fixed oils. Intravenous vehicles include liquid and nutrient supplements, electrolyte supplements and the like. Preservatives and other additives may also be present, for example, such as antimicrobial agents, antioxidants, chelating agents and inert gases.

The medical staff will determine the dosage regimen based on various clinical factors. As is well known in the medical field, the dosage of any patient depends on a variety of factors, including the patient's size, body surface area, age, the specific compound to be administered, sex, frequency and route of administration, overall health and other drugs administered simultaneously. The dosage range of the pharmaceutical composition comprising plasminogen of the present invention may be, for example, such as about 0.0001 to 2000 mg/kg, or about 0.001 to 500 mg/kg (such as 0.02 mg/kg, 0.25 mg/kg, 0.5 mg/kg, 0.75 mg/kg, 10 mg/kg and 50 mg/kg) of the subject's body weight daily. For example, the dosage may be 1 mg/kg body weight or 50 mg/kg body weight, or in the range of 1 mg/kg-50 mg/kg, or at least 1 mg/kg. Dosages above or below this exemplary range are also contemplated, especially considering the above factors. The intermediate dosages in the above range are also included in the scope of the present invention. A subject may be administered with such dosages daily, every other day, weekly or based on any other schedule determined by empirical analysis. An exemplary dosage schedule includes 1-10 mg/kg for consecutive days. During administration of the drug of the present invention, the therapeutic effect and safety are required to be assessed real-timely.

A Product or a Kit

One embodiment of the present invention relates to a product or a kit comprising the plasminogen or plasmin for treat osteoarthritis according to the present invention. The product preferably comprises a container, label or package insert. Suitable containers include bottles, vials, syringes and the like. The container can be made of various materials, such as glass or plastic. The container contains a composition that is effective to treat the disease or disorder of the present invention and has a sterile access (for example, the container may be an intravenous solution bag or vial containing a plug that can be pierced by a hypodermic injection needle). At least one active agent in the composition is plasminogen/plasmin. The label on or attached to the container indicates that the composition is used for treating the osteoarthritis according to the present invention. The article of manufacture may further comprise a second container containing a pharmaceutically acceptable buffer, such as phosphate buffered saline, Ringer's solution and glucose solution. It may further comprise other substances required from a commercial and user perspective, including other buffers, diluents, filters, needles and syringes. In addition, the article of manufacture comprises a package insert with instructions for use, including, for example, instructions to a user of the composition to administer the plasminogen composition and other drugs to treat an accompanying disease to a patient.

BRIEF DESCRIPTION OF THE DRAWINGS

FIG. 1A is from the blank control group, FIG. 1B is from the vehicle (PBS) control group, FIG. 1C is from the plasminogen group, and FIG. 1D is the quantitative analysis result. The results show that the knee cartilage (marked by arrow) in the plasminogen group is significantly more than that of the vehicle (PBS) control group, and the statistical difference is significant (* indicates P<0.05); and compared with the vehicle (PBS) control group, in the plasminogen group the amount of knee cartilage is closer to that of the mice in the blank control group. It indicates that plasminogen can significantly reduce the loss of cartilage in the knee joints of the aging model mice induced by vitamin D.

FIG. 2A and FIG. 2C are from the vehicle (PBS) control group, FIG. 2B and FIG. 2D are from the plasminogen group, and E is the quantitative analysis result. The results show that the pathological score of the knee joints in the plasminogen group is significantly lower than that in the vehicle (PBS) control group, and the statistical difference is extremely significant (** indicates P<0.01). It indicates that plasminogen can alleviate the knee joint injury of osteoarthritis model mice induced by type II collagenase.

FIG. 3A and FIG. 3C are from the vehicle (PBS) control group, and FIG. 3B and FIG. 3D are from the plasminogen group. The results show that the structural arrangement of cartilage tissue (thin arrow marked) in the vehicle (PBS) control group is disordered, the number of cells is significantly reduced, the staining of Safranin O is significantly reduced, and the bone trabecula (thick arrow marked) became thinner and broken. Compared with the vehicle (PBS) control group, in the plasminogen group the cartilage tissue structure is relatively neat, the number of cells in the cartilage is relatively large, and the staining range of safranin O is relatively wide. It indicates that plasminogen can reduce the knee joint injury of osteoarthritis PIg$^{-/-}$ mice induced by type II collagenase.

FIG. 4A is from the vehicle (PBS) control group, and FIG. 4B is from the plasminogen group. The results show that in the vehicle (PBS) control group, the cartilage (triangle marked) is severely lost, and the bone trabecula (arrow marked) becomes thinner and broken, and there is a large area of the marrow cavity without bone trabecula; and compared with the vehicle (PBS) control group, in the plasminogen group the bone trabecula has good continuity, no severe fracture, no large area of the region without bone trabecula, and relatively more cartilage tissue. It indicates that plasminogen can improve the knee joint tissue structure of osteoarthritis model mice induced by ligament transection.

FIG. 5A and FIG. 5C are from the vehicle (PBS) control group, FIG. 5B and FIG. 5D are from the plasminogen group, and FIG. 5E is from the quantitative analysis result. The results show that the alkaline phosphatase staining of the knee cartilage surface (thin arrow marked) and growth plate (thick arrow marked) of the plasminogen group mice is more than that of the vehicle (PBS) control group, and the statistical difference is significant (* indicates $P<0.05$). It indicates that plasminogen can significantly promote the increase of alkaline phosphatase activity in the knee joints of osteoarthritis model mice induced by ligament transection, that is, plasminogen promotes the activity of knee cartilage osteoblast to increase significantly.

FIG. 6A is from the sham operation group, FIG. 6B is from the vehicle control group, FIG. 6C is from the plasminogen group, and FIG. 6D is the quantitative analysis result. The results show that there is a certain amount of type II collagen (arrow marked) in the knee joint of the sham operation group; the amount of type II collagen in the knee joint of the vehicle control group is not significantly different from that of the sham operation group, while the amount of type II collagen of the plasminogen group is significantly higher than that of the vehicle control group and the sham operation group, and the statistical difference of quantitative analysis of the average optical density is significant (* indicates $P<0.05$). The results show that plasminogen can promote the regeneration of knee cartilage in osteoarthritis model mice.

FIG. 7A is from the sham operation group, FIG. 7B is from the vehicle control group, FIG. 7C is from the plasminogen group, and FIG. 7D is the pathological scoring result. The results show that there is a certain amount of cartilage in the knee joint of the sham operation group (arrow marked) the amount of knee cartilage in the vehicle control group is significantly reduced and the pathological score is significantly increased, indicating that MIA successfully induces osteoarthritis; the amount of knee cartilage in the plasminogen group is significantly higher than that in the vehicle control group, and the pathological scores are also significantly lower than those in the vehicle control group, and the statistical difference is significant (* indicates $P<0.05$). This result indicates that plasminogen can promote cartilage regeneration and improve osteoarthritis injury.

FIG. 8A is from the sham operation group, FIG. 8B is from the vehicle control group, FIG. 8C is from the plasminogen group, and FIG. 8D is the quantitative analysis result of average optical density. The results show that there is a small amount of cartilage (marked by arrows) on the femoral surface of the knee joints in the sham operation group; there is no significant difference between the amount of cartilage on the femoral surface in the vehicle control group and that in the sham operation group, while the amount of cartilage on the femoral surface in the plasminogen group is significantly higher than that in the vehicle control group and the sham operation group, and the statistical difference of quantitative analysis results of average optical density is significant (* indicates $P<0.05$). The results show that plasminogen can promote the regeneration of cartilage on the femoral surface of osteoarthritis model mice.

EXAMPLES

Example 1: Plasminogen Reduces Cartilage Loss in Knee Joints of Vitamin D Induced Osteoporosis Mice Fifteen 5-6 weeks aged male C57 mice are taken, and randomly divided into 3 groups after weighing, i.e., a blank control group, a plasminogen group, and a vehicle (PBS) control group; 5 mice in each group. The mice in the blank control group are injected intraperitoneally with 50 µl of corn oil every day: the mice in the plasminogen group and the vehicle (PBS) control group are injected intraperitoneally with vitamin D (Sigma Aldrich) at 0.5 µg/kg body weight every day to induce osteoporosis model [6, 27]. At the same time, administration to the mice starts. The human plasminogen is injected into the tail vein of the plasminogen group mice at 1 mg/0.1 mL/mouse/day, and the same volume of PBS is injected into the tail vein of the vehicle (PBS) control group mice, the mice in the blank control group are not administered, and the administration is taken 28 consecutive days to generate the model. During the administration period, all mice are fed with low calcium feed. The first day of model generation and medicine administration is set as day 1, after being sacrificed on day 29, the knee joints are taken and fixed with 4% paraformaldehyde for 24 hours, then decalcifying in 10% EDTA for three weeks, and washing with gradient sucrose solution the above operations need to be operated at 4° C. condition. Then the samples are embedded in paraffin, cut into 8 µm sections and stained with safranin O. The sections are observed under a 100× optical microscope.

The staining principle of cartilage staining solution (safranin O method) lies in that: the basophilic cartilage is combined with the basic dye safranin O to show a red color safranin O is a cationic dye combined with multiple anions, and revealing of cartilage by safranin O is based on the fact that cationic dyes will combine with the anionic groups in polysaccharide (chondroitin sulfate or keratan sulfate). Safranin O color density is approximately proportional to the anion concentration, indirectly reflecting the content and distribution of proteoglycans in the matrix.

Safranin O staining, namely safranin staining, mainly shows the acidic proteoglycan component in cartilage tissue, and it can show the formation of cartilage [28].

Figure 1:
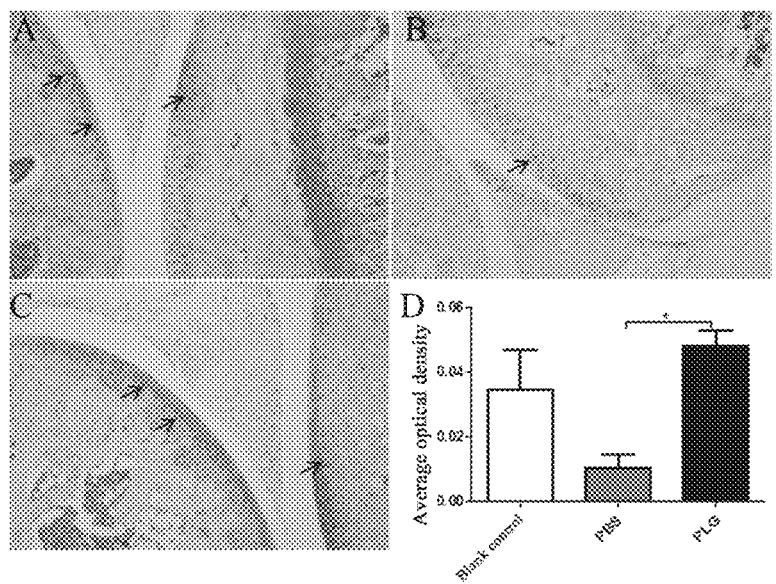
FIGS. 1A-1D show the Safranin O staining results of knee joints in the aging model mice induced by 0.5 μg/kg vitamin D.

The results show that the knee cartilage (marked by arrows) in the plasminogen group (FIG. 1C) is significantly more than that in the vehicle (PBS) control group (FIG. 1B), and the statistical difference is significant (* indicates P<0.05) (FIG. 1D); compared with the vehicle (PBS) control group, the knee cartilage in the plasminogen group is closer to that in the blank control mice (FIG. 1A). This indicates that plasminogen can significantly reduce the cartilage loss in the knee joints of vitamin D induced osteoporosis model mice.

Example 2: Plasminogen Reduces Knee Joint Injury in Osteoarthritis Model Mice Induced by Type II Collagenase Twelve 10-week-old C57 male mice are injected intraperitoneally with pentobarbital sodium at 50 mg/kg body weight, then anesthetizing the mice, and intramuscularly injecting Tolfedine (0.1 ml/kg). A gap is made in the right knee joint of a mouse, and the knee joint is bent 90 degrees, then the articular cavity of the mouse is injected with type II collagenase (C6885, sigma) at 5 µg/6 µl per mouse; the left knee joint is treated identically to the right knee joint, but only the same volume of normal saline is injected [29,30]. Seven days after the injection, the mice are randomly divided into two groups according to their body weights, 6 mice in each group for the vehicle (PBS) control group and the plasminogen group; then the administration starts. The human plasminogen is administered to the plasminogen group mice by tail vein injection at 1 mg/0.1 ml/mouse/day, and the same volume of PBS is injected into the tail vein of the vehicle (PBS) control group mice for 14 consecutive days. The first day of administration is set as day 1, after being sacrificed on day 15, the knee joints are taken and fixed with 4% paraformaldehyde for 24 hours, then decalcifying in 10% EDTA for three weeks, and washing with gradient sucrose solution: the above operations need to be operated at 4° C. condition. Then the samples are embedded in paraffin, sectioned at 8 µm and stained with safranin O. The sections are observed under 40× (A, B) and 100× (C, D) optical microscopes, and the pathological scores of the knee joints are evaluated according to the following Table 1 [31].

TABLE 1

| Types | Subtypes | Scores |
| --- | --- | --- |
| Structure of the soft tissues | Normal | 0 |
| | unorganized, but the layer are distinguishable. | 1 |
| | apparently unorganized, and the layers are disordered. | 2 |
| | Significantly disordered | 3 |
| Number of the cartilage cells | Normal | 0 |
| | Slight reduction | 1 |
| | Moderate reduction | 2 |
| | Severe reduction | 3 |
| Safranin O staining | Normal | 0 |
| | Slight decrease | 1 |
| | Moderate decrease | 2 |
| | Severe decrease | 3 |
| | Non-staining | 4 |
| Tidemark | Normal | 0 |
| | Uncompleted | 1 |
| Total score | | 0-11 |

Figure 2:
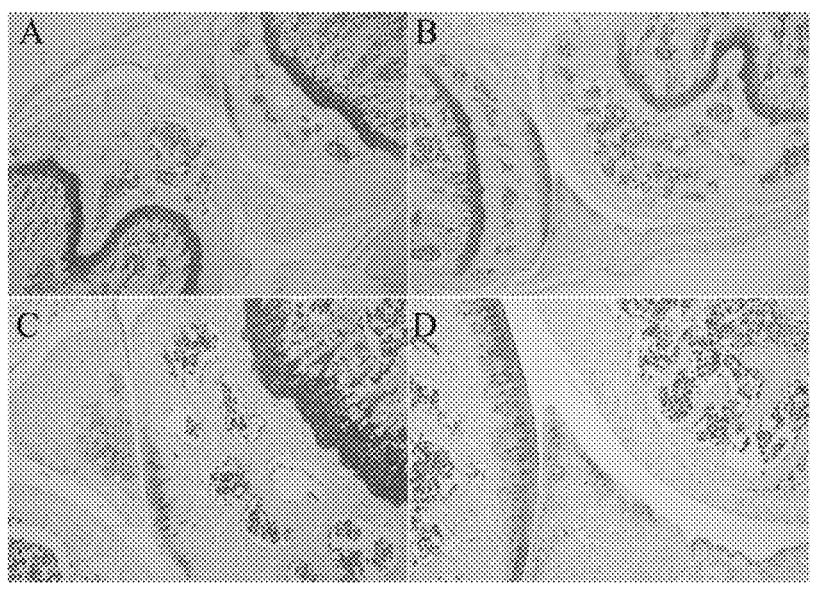
FIGS. 2A-2E: Scoring results of Safranin O staining of knee joints in osteoarthritis model mice induced by type II collagenase 14 days after the administration of plasminogen.

The results show that the pathological scores of the knee joints in the plasminogen group (FIGS. 2B, D) are significantly lower than those in the vehicle (PBS) control group (FIGS. 2A, C), and the statistical difference is extremely significant (** indicates P<0.01) (FIG. 2E). It indicates that plasminogen can significantly reduce the knee joint injury of type II collagenase induced osteoarthritis, and reduce the loss of articular cartilage.

Example 3: Plasminogen Improves the Structure States of Knee Joint Tissues in Osteoarthritis Model PIg$^{-/-}$ Mice Induced by Type II Collagenase Ten 10-week-old PIg$^{-/-}$ male mice are intraperitoneally injected with pentobarbital sodium at 50 mg/kg body weight, then anesthetizing the mice, and intramuscularly injecting Tolfedine (0.1 ml/kg). A gap is made in the right knee joint of a mouse, and the knee joint is bent 90 degrees, then the articular cavity of the mouse is injected with type II collagenase (C6885, sigma) at 5 μg/6 μl per mouse; the left knee joint is treated identically to the right knee joint, but only the same volume of normal saline is injected [29,30]. Seven days after the injection, the mice are randomly divided into two groups according to their body weights, 5 mice in each group for the vehicle (PBS) control group and the plasminogen group; then the administration starts. The human plasminogen is administered to the plasminogen group mice by tail vein injection at 1 mg/0.1 ml/mouse/day, and the same volume of PBS is injected into the tail vein of the vehicle (PBS) control group mice for 14 consecutive days. The first day of administration is set as day 1, after being sacrificed on day 15, the knee joints are taken and fixed with 4% paraformaldehyde for 24 hours, then decalcifying in 10% EDTA for three weeks, and washing with gradient sucrose solution: the above operations need to be operated at 4° C. condition. Then the samples are embedded in paraffin, sectioned at 8 μm and stained with safranin O. The sections are observed under 40× (A, B) and 100× (C, D) optical microscopes.

Figure 3:
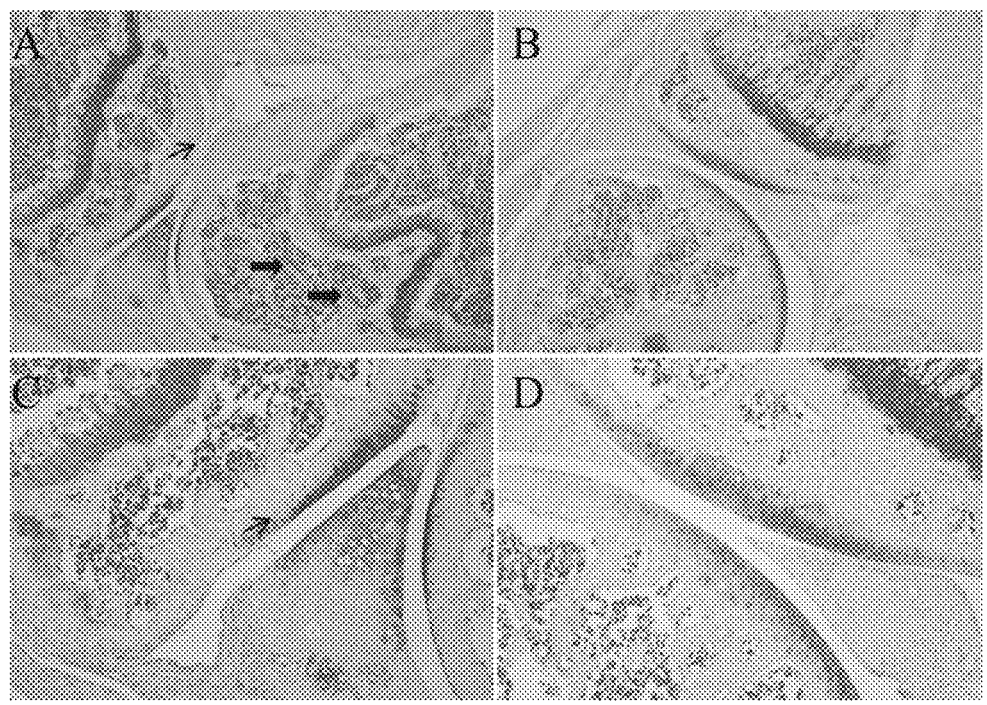
FIGS. 3A-3D: Representative Safranin O staining pictures of the knee joints in the osteoarthritis model PIg$^{-/-}$ mice induced by type II collagenase 14 days after the administration of plasminogen.

The results show that in the vehicle (PBS) control group (FIGS. 3A, C), the structural arrangement of the cartilage tissue (thin arrow marked) is disordered, the number of cells is significantly reduced, safranin O staining is significantly reduced, and the bone trabecula (thick arrow marked) becomes thinner and broken compared with the vehicle (PBS) control group, the plasminogen group (FIGS. 3B, D) has relatively neat cartilage tissue structure, relatively large numbers of cells in the cartilage, and a relatively wide staining range for safranin O. It indicates that plasminogen can reduce the knee joint injury of osteoarthritis PIg$^{-/-}$ mice induced by type II collagenase.

Example 4: Plasminogen Improves the Structural States of the Knee Joint Tissues in Osteoarthritis Model Mice Induced by Ligament Transection Ten 9-10 weeks aged male C57 mice are injected intraperitoneally with pentobarbital sodium at 50 mg/kg body weight, then anesthetizing the mice. The hair around the knee joint is removed, and Tolfedine (0.1 ml/kg) analgesic is intramuscularly injected into a mouse immediately before surgery. The mouse is placed under a dissecting microscope, and a gap is made at the distal end of the right patella and tibial plateau to separate the patellar ligament and expose the articular cavity; bluntly separating the fat pad between the femoral condyles so that the anterior cruciate ligament can be observed; cutting the anterior cruciate ligament and inside collateral ligament with microblade, and sewing the joint capsule and skin to establish an osteoarthritis model [33,33]. As for the left knee joint, only the articular cavity is exposed and the transection operation is not performed. Care should be taken to avoid damaging the articular cartilage during the operation, the limbs are not fixed after the operation, and mice can move freely in the cage. On the first day after the surgery, the mice are injected intramuscularly with Tolfedine (0.1 mg/kg) and potassium penicillin (40,000 units/kg) every 12 hours. Two weeks later, the mice are randomly divided into two groups according to their body weights, 5 mice in each group for the vehicle (PBS) control group and the plasminogen group then the administration to the mice starts. The human plasminogen is administered to the plasminogen group mice by tail vein injection at 1 mg/0.1 ml/mouse/day, and the same volume of PBS is injected into the tail vein of the vehicle (PBS) control group mice for 14 consecutive days. The first day of administration is set as day 1, after being sacrificed on day 15, the knee joints are taken and fixed with 4% paraformaldehyde for 24 hours, then decalcifying in 10% EDTA for three weeks, and washing with gradient sucrose solution the above operations need to be operated at 4° C. condition. Then the samples are embedded in paraffin, sectioned at 4 μm and stained with safranin O. The sections are observed under a 40× optical microscope.

Figure 4:
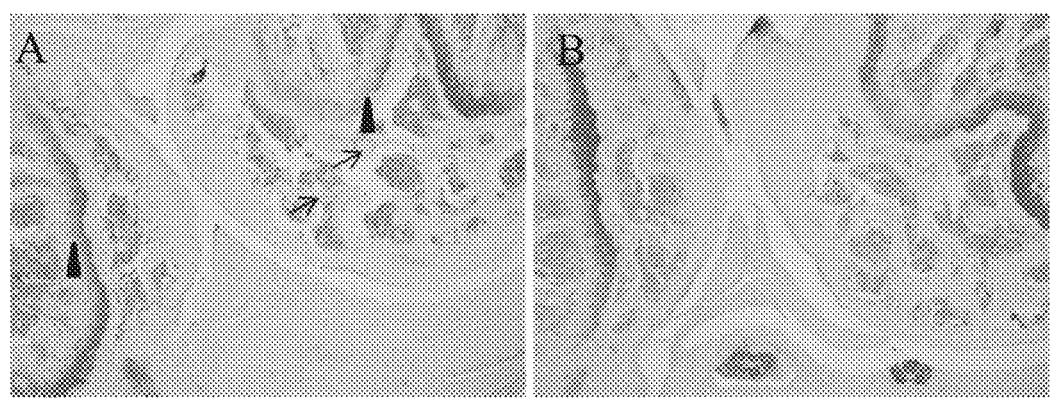
FIGS. 4A-4B: Representative Safranin O staining pictures of the knee joints in the osteoarthritis model mice induced by ligament transection 14 days after the administration of plasminogen.

The results show that in the vehicle (PBS) control group (FIG. 4A), the cartilage (triangle marked) is severely lost, and the bone trabecula (arrow marked) becomes thinner and broken, and there is a large area of the marrow cavity without bone trabecula; and compared with the vehicle (PBS) control group, in the plasminogen group (FIG. 4B) the bone trabecula has good continuity, no severe fracture, no large area of the region without bone trabecula, and relatively more cartilage tissue. It indicates that plasminogen can improve the knee joint tissue structure of osteoarthritis model mice induced by ligament transection.

Example 5: Plasminogen Increases Alkaline Phosphatase Activity in the Knee Joints of Osteoarthritis Model Mice Induced by Ligament Transection Ten 9-10 weeks aged male C57 mice are injected intraperitoneally with pentobarbital sodium at 50 mg/kg body weight, then anesthetizing the mice. The hair around the knee joint is removed, and Tolfedine (0.1 ml/kg) analgesic is intramuscularly injected into a mouse immediately before surgery. The mouse is placed under a dissecting microscope, and a gap is made at the distal end of the right patella and tibial plateau n separate the patellar ligament and expose the articular cavity: bluntly separating the fat pad between the femoral condyles so that the anterior cruciate ligament can be observed cutting the anterior cruciate ligament with microblade, and sewing the joint capsule and skin to establish an osteoarthritis model [32,33]. As for the left knee joint, only the articular cavity is exposed and the transection operation is not performed. Care should be taken to avoid damaging the articular cartilage during the operation, the limbs are not fixed after the operation, and mice can move freely in the cage. On the first day after the surgery, the mice are injected intramuscularly with Tolfedine (0.1 mg/kg) and potassium penicillin (40,000 units/kg) every 12 hours. Two weeks later, the mice are randomly divided into two groups according to their body weights, 5 mice in each group for the vehicle (PBS) control group and the plasminogen group; then the administration to the mice starts. The human plasminogen is administered to the plasminogen group mice by tail vein injection at 1 mg/0.1 ml/mouse/day, and the same volume of PBS is injected into the tail vein of the vehicle (PBS) control group mice for 14 consecutive days. The first day of administration is set as day 1, after being sacrificed on day 15, the knee joints are taken and fixed in fixative. The fixative formula: 2% paraformaldehyde, 0.075 mol/L lysine, 0.01 mol/L sodium periodate. After fixation, gradient washing is performed for each sample with PBS solution at 4° C. for 12 hours, and then placing in 4° C. decalcifying solution for 2 weeks, and the decalcifying solution is changed every 5 days. After decalcification is completed, gradient washing is performed for each sample with PBS solution at 4° C. for 12 hours, and then the knee joint is dehydrated with alcohol gradient, made transparent with xylene, and embedded in paraffin. 5 μm sections are cut, dewaxing and rehydrating, and incubating with magnesium chloride buffer at 4° C. overnight. Then the sections are incubated in alkaline phosphatase substrate solution for 1 hour at room temperature, counterstaining with hematoxylin for 2 min, rinsing in running water for 5 min, baking at 60° C. for 30 min, sealing with neutral gum, and then observing the sections under a 200× optical microscope.

Alkaline phosphatase (ALP) is a marker of early differentiation of osteoblasts [32].

Figure 5:
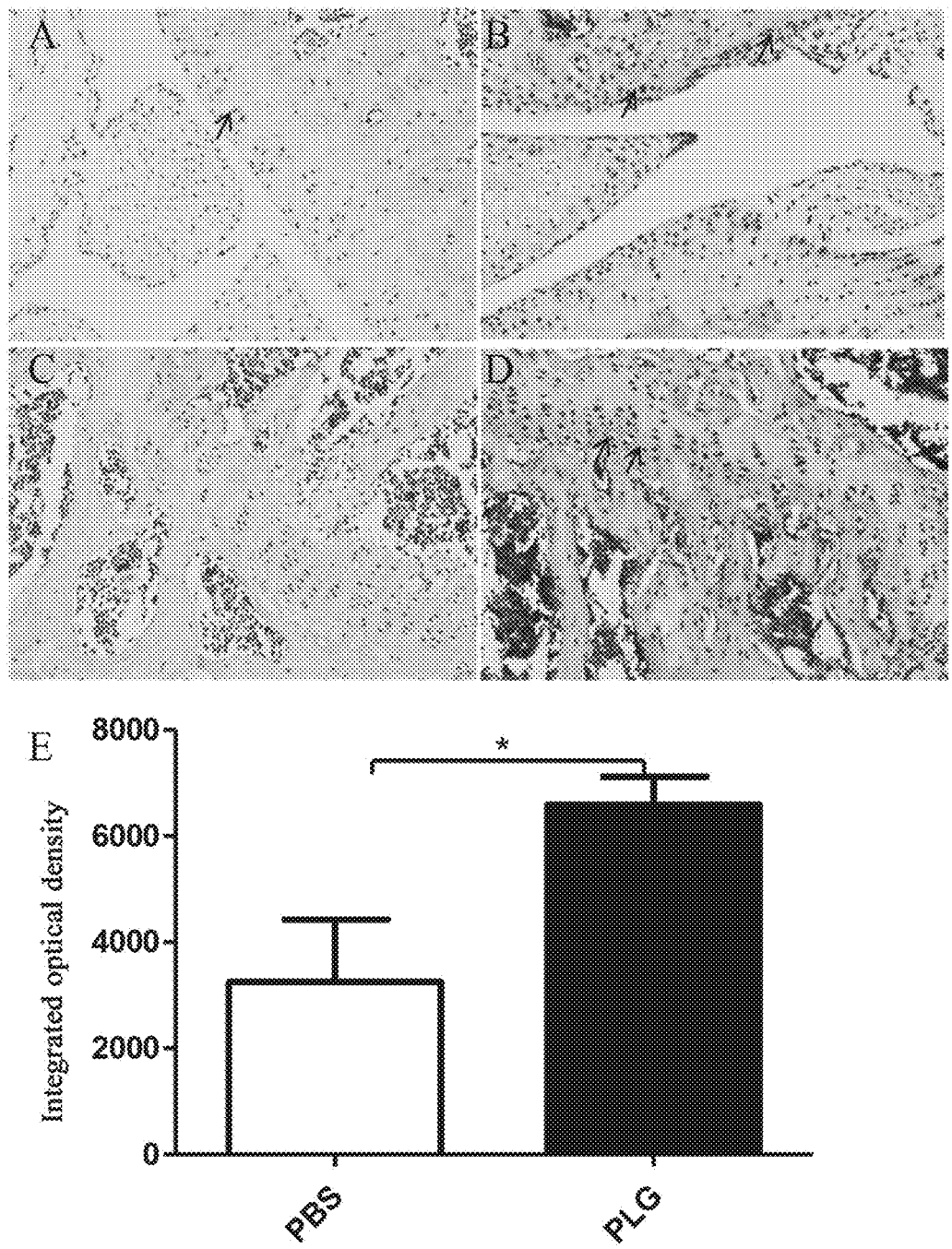
FIGS. 5A-5E: Results of alkaline phosphatase staining of the knee joints in the osteoarthritis model mice induced by ligament transection 14 days after the administration of plasminogen.

The results show that the alkaline phosphatase staining (arrow marked) on the surface of the knee cartilage and the growth plate of the plasminogen group mice (FIGS. 5B, D) is more than that in the vehicle (PBS) control group mice (FIGS. 5A, C), and the statistical difference is significant (* indicates P<0.05) (FIG. 5E). It indicates that plasminogen can significantly promote the increase of alkaline phosphatase activity in the knee joints of osteoarthritis model mice induced by ligament transection, that is, plasminogen promotes the osteoblast activity of knee cartilage to increase significantly.

Example 6: Plasminogen Promotes the Regeneration of Knee Cartilage in MIA Osteoarthritis Model Mice Twenty five 8-10 weeks aged C57 male mice are weighed and randomly divided into two groups according to body weights; 5 mice in the sham operation group, and 20 mice in the model group. All mice are anesthetized by intraperitoneal injection of 3% pentobarbital sodium at 50 mg/kg body weight. After anesthesia, for the mice in the model group, the hair of the left knee is removed, disinfecting with 70% alcohol and iodine tincture: and the left knee joint is bent 90 degrees, moving the needle of the syringe horizontally along the knee (so as not to pierce the skin) until a gap under the patella is found marking the area with slight pressure, then lifting the needle and syringe vertically, inserting the needle into the marked area, through the patellar tendon perpendicular to the tibia, and MIA (monoiodoacetic acid) physiological saline solution is injected into the articular cavity at 0.1 mg/10 μl; in the sham operation group, 10 μl saline is injected into the left articular cavity, after the injection, massaging the knee to ensure even distribution [34]. The right knee joint is not treated. Three days after the MIA injection in the articular cavity, the mice in the model group are subjected to a pain test. According to the test results, the mice are randomly divided into two groups: 10 mice in each group for the vehicle control group and the plasminogen group; then the drugs are administered to the mice, and the day of first administration is set as day 1. The human plasminogen is administered to the plasminogen group mice by tail vein injection at 1 mg/0.1 ml/mouse/day, and the same volume of PBS buffer is injected into the tail vein of the vehicle (PBS) control group mice for 28 consecutive days. The mice in the sham operation group are not administered. The preparation of MIA solution: MIA powder (Sigma. 57858-5G) is dissolved in physiological saline at a concentration of 10 mg/ml, and then filtering with a 0.22 μm filter membrane, and using right after it is ready. The mice are sacrificed on day 29, and the left knee joints are taken and fixed in PLP fixative solution, then decalcifying in 10% EDTA for three weeks, washing with gradient sucrose solution, and embedding in paraffin. The thickness of the tissue section is 5 μm, and the sections are washed once after dewaxing and rehydrating. The tissues are circled with a PAP pen, then incubating with 3% hydrogen peroxide for 15 min, and washing twice with 0.01M PBS for 5 min each time. 5% normal sheep serum (Vector laboratories, Inc., USA) is used to block for 30 min after the time is expired, the sheep serum is discarded, then adding rabbit-derived anti-type II collagen antibody (Abcam, ab34712) dropwise, incubating overnight at 4° C., and washing twice with 0.01M PBS for 5 min each time. Goat anti-rabbit IgG (HRP) antibody (Abcam) (secondary antibody) is incubated for 1 hour at room temperature, then washing twice with 0.01M PBS for 5 min each time. Color development is performed according to the DAB kit (Vector laboratories, Inc., USA), after washing three times with water, counterstaining with hematoxylin for 30 seconds, and rinsing under running water for 5 min. Dehydration is performed with gradient alcohol, then making transparent with xylene and sealing with neutral gum: and the sections are observed and photographed under a 200× optical microscope, processing with Image-Pro software to collect data.

Monoiodoacetic acid (MIA) has the effect of destroying articular cartilage and the surrounding synovial ligaments the original steady state of the articular cavity may be changed by injecting MIA into the articular cavity, and an intra-articular inflammatory reaction may also be triggered, thereby changing the metabolism of the cartilage and the subchondral bone, destroying the stability of the environment in the joints, and causing chondrocyte apoptosis and cartilage wear. Studies have shown that monoiodoacetic acid can inhibit the metabolism of articular chondrocytes, causing the death of chondrocytes, which in turn leads to the degradation of cartilage matrix, inducing arthritis cartilage changes and osteoarthritis models. Type II collagen is one of the main components of cartilage matrix, and plays an important role in maintaining the mechanical properties of cartilage [35].

Figure 6:
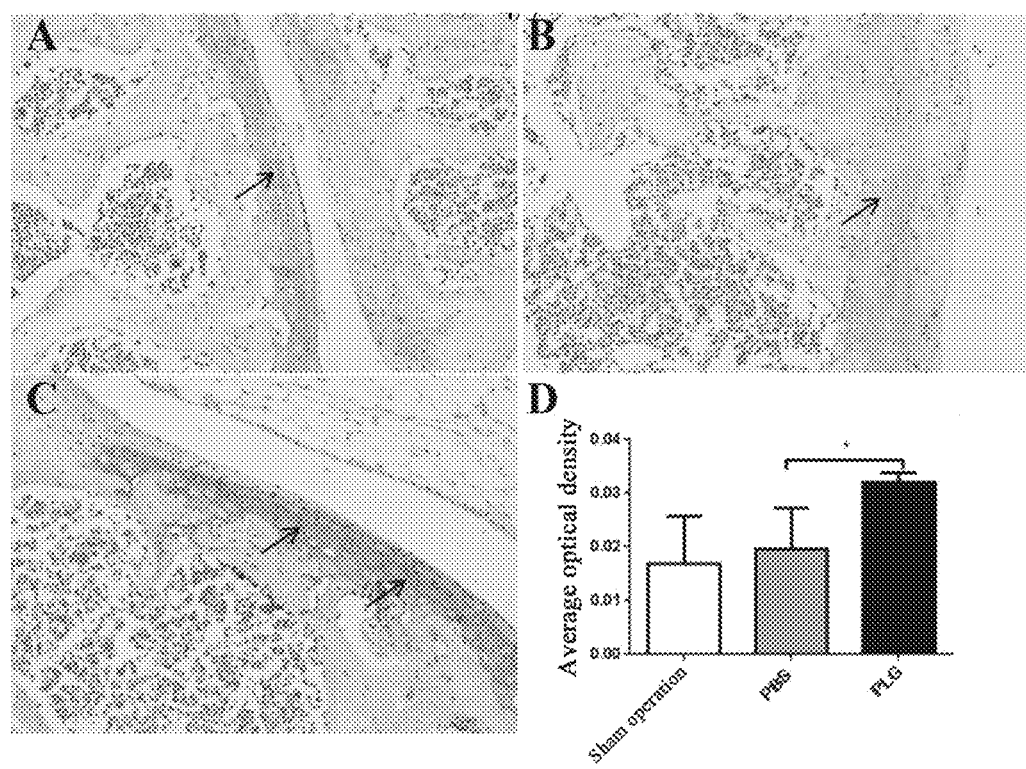
FIGS. 6A-6D: Results of immunohistochemical staining of type II collagen in the knee joint of MIA osteoarthritis model mice 28 days after the administration of plasminogen.

The results show that there is a certain amount of type II collagen (marked by arrow) in the knee joints of the sham operation group mice (FIG. 6A); the amount of type II collagen in the knee joints of the vehicle control group mice (FIG. 6B) is not significantly different from that of the sham operation group mice, while the amount of type II collagen in the knee joints of the plasminogen group mice (FIG. 6C) is significantly higher than that of the vehicle control group and the sham operation group mice, and the statistical difference of the quantitative analysis result of the average optical density is significant (* indicates P<0.05) (FIG. 6D). The results show that plasminogen can promote the regeneration of knee cartilage in osteoarthritis model mice.

Example 7: Improvement Effect of Plasminogen on MIA-Induced Osteoarthritis

Twenty five 8-10 weeks aged C57 male mice are weighed and randomly divided into two groups according to body weights; 5 mice in the sham operation group, and 20 mice in the model group. All mice are anesthetized by intraperitoneal injection of 3% pentobarbital sodium at 50 mg/kg body weight. After anesthesia, for the mice in the model group, the hair of the left knee is removed, disinfecting with 70% alcohol and iodine tincture; and the left knee joint is bent 90 degrees, moving the needle of the syringe horizontally along the knee (so as not to pierce the skin) until a gap under the patella is found marking the area with slight pressure, then lifting the needle and syringe vertically, inserting the needle into the marked area, through the patellar tendon perpendicular to the tibia, and MIA physiological saline solution is injected into the articular cavity at 0.1 mg/10 μl; in the sham operation group, 10 μl saline is injected into the left articular cavity, after the injection, massaging the knee to ensure even distribution [34]. The right knee joint is not treated. Three days after the MIA injection in the articular cavity, the mice in the model group are subjected to a pain test. According to the test results, the mice are randomly divided into two groups: 10 mice in each group for the vehicle control group and the plasminogen group then the administration starts, and the day of first administration is set as day 1. The human plasminogen is administered to the plasminogen group mice by tail vein injection at 1 mg/0.1 ml/mouse/day, and the same volume of PBS buffer is injected into the tail vein of the vehicle (PBS) control group mice for 28 consecutive days. The mice in the sham operation group are not administered. The preparation of MIA solution: MIA powder (Sigma, 57858-5G) is dissolved in physiological saline at a concentration of 10 mg/ml, and then filtering with a 0.22 μm filter membrane, and using right after it is ready. The mice are sacrificed on day 29, and the left knee joints are taken and fixed in PLP fixative solution, then decalcifying in 10% EDTA for three weeks, washing with gradient sucrose solution, and embedding in paraffin. The 5 μm sections are stained with safranin O. The sections are observed and photographed under a 40× optical microscope, and the pathological scores are evaluated according to Table 1.

Figure 7:
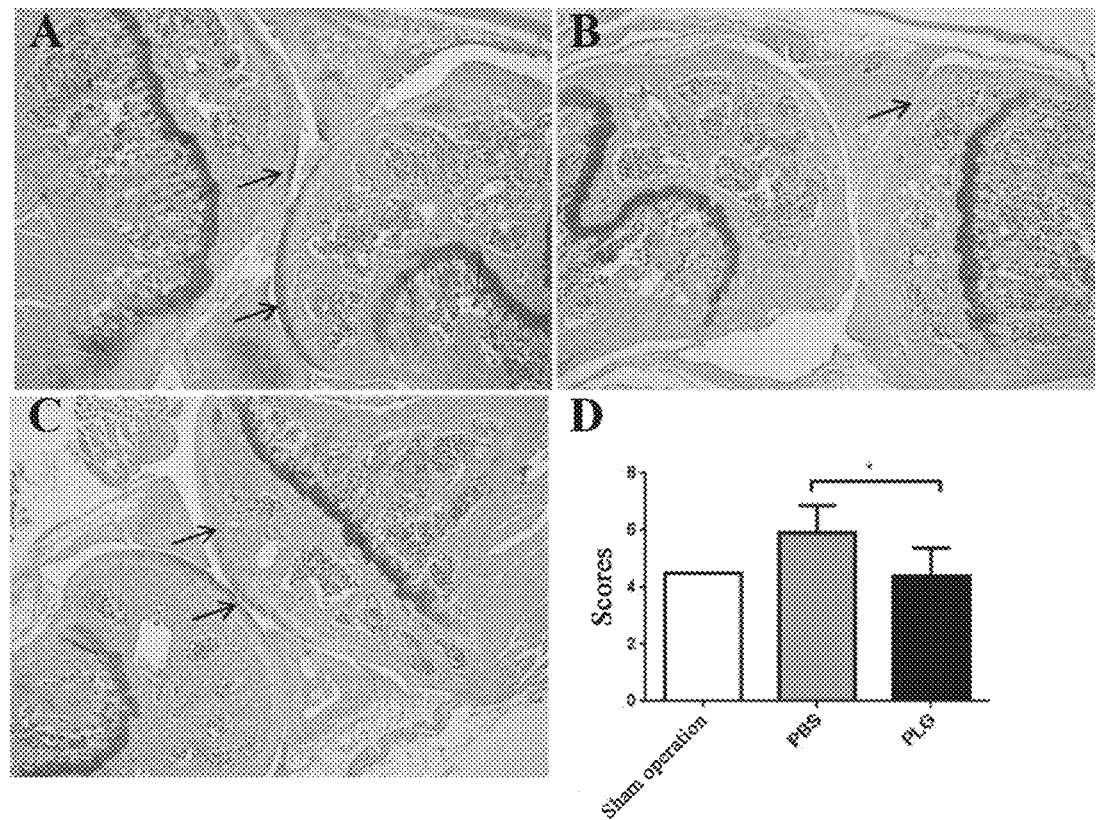
FIGS. 7A-7D: Representative Safranin O staining pictures of the knee joint of MIA osteoarthritis model mice 28 days after the administration of plasminogen.

The results show that there is a certain amount of cartilage in the knee joints of the sham operation group mice (FIG. 7A) (marked by arrows): for the vehicle control group (FIG. 7B), the amount of knee cartilage is significantly reduced, and the pathological scores are significantly increased, indicating that MIA successfully induces osteoarthritis: the amount of cartilage in the knee joints of the plasminogen group mice (FIG. 7C) is significantly more than that in the vehicle control group, and the pathological scores are also significantly lower than those in the vehicle control group, and the statistical difference is significant (* indicates P<0.05) (FIG. 7D). This result indicates that plasminogen can promote cartilage regeneration and repair the articular injury caused by osteoarthritis.

Example 8: Plasminogen Promotes Regeneration of Knee Cartilage in Osteoarthritis Model Mice Eighteen 11-15 weeks aged female db/db mice are weighed and randomly divided into two groups according to body weights, 3 mice in the sham operation group and 15 mice in the model group. The mice in the model group are anesthetized by intraperitoneal injection of 3% pentobarbital sodium at 50 mg/kg body weight the hair on both sides of the back is removed, disinfecting with 70% alcohol and iodine tincture: the skin, back muscles and peritoneum are cut open, and the white shiny fat tissue is gently pulled out through the incision by using small forceps so as to separate the fat tissue, and the ovaries can be seen. The fallopian tube at the lower end of ovary is ligated with silk thread, and then the ovary is removed. After anesthesia, for the mice in the sham operation group, only the skin, back muscles and peritoneum are cut open, and the ovaries are not removed. After suture and disinfection, all surgical mice are intramuscularly injected with antibiotics (5000U/mouse), and subcutaneously injected with analgesic (2 mg/kg). The injection is taken for 3 consecutive days. 65 days after the ovariectomy, all mice are intraperitoneally injected with pentobarbital sodium for anesthesia, removing the hair on the right knee, disinfecting with 70% alcohol and iodine tincture; the right knee is bent 90 degrees to find the precise injection site, moving the needle of the syringe along the knee horizontally (so as not to pierce the skin) until a gap under the patella is found; marking the area with slight pressure, then lifting the needle and syringe vertically, inserting the needle into the marked area, though the patellar tendon perpendicular to the tibia and no resistance should be felt. As for the model group mice, 5 μg/6 μl Type II collagenase physiological saline solution is injected into the right articular cavity of the mice; as for the sham operation group mice, 6 μl of physiological saline is injected into the right articular cavity of the mice [36,37]. After the injection, the knee is massaged to ensure even distribution. The left knee joint is not treated with injection. 7 days after the collagenase injection, all mice are weighed. The mice in the model group are randomly divided into two groups according to their body weights, 7 mice in the vehicle control group and 8 mice in the plasminogen group: then the administration starts, and the day of first administration is set as day 1. The human plasminogen is administered to the plasminogen group mice by tail vein injection at 1 mg/0.1 ml/mouse/day, and the same volume of PBS buffer is injected into the tail vein of the vehicle control group mice for 28 consecutive days. The mice in the sham operation group are not administered. The mice are sacrificed on day 29, and the left knee joints are taken and fixed in PLP fixative solution, then decalcifying in 10% EDTA for three weeks, washing with gradient sucrose solution, and embedding in paraffin. The 5 μm sections are stained with safranin O. The sections are observed and photographed under a 100× optical microscope, processing with Image-Pro software to collect data.

Figure 8:
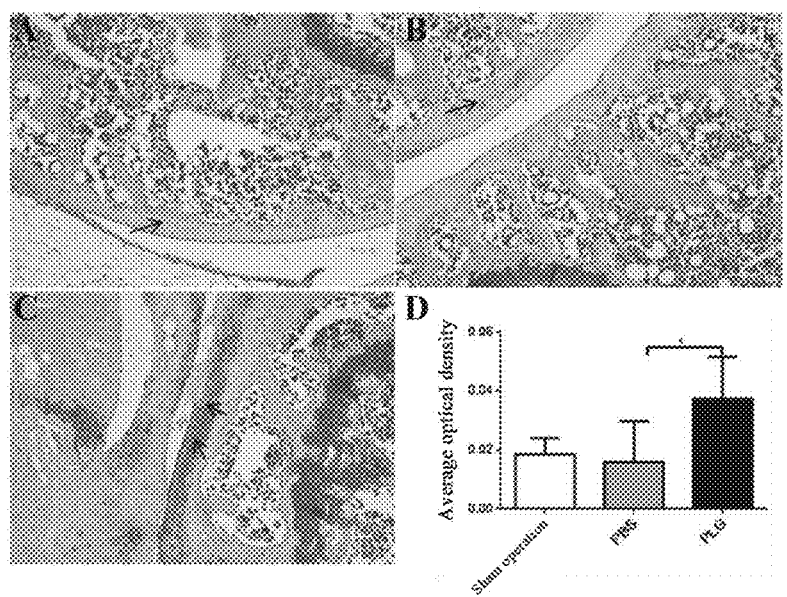
FIGS. 8A-8D: Results of Safranin 0 staining on the femoral surface of the left knee joint of the osteoarthritis model mice 28 days after the administration of plasminogen.

The results show that there is a small amount of cartilage (marked by arrows) on the femoral surface of the knee joints in the sham operation group mice (FIG. 8A); there is no significant difference between the amount of cartilage on the femoral surface in the vehicle control group (FIG. 8B) and that in the sham operation group, while the amount of cartilage on the femoral surface in the plasminogen group (FIG. 8C) is significantly higher than that in the vehicle control group and the sham operation group, and the statistical difference of quantitative analysis of the average optical density is significant (* indicates P<0.05) (FIG. 8D). The results show that plasminogen can promote the regeneration of cartilage on the femoral surface of osteoarthritis model mice.

Example 9: Plasminogen Reduces Arthritis Pain in MIA Osteoarthritis Model Rats

Twenty-one SD rats are weighed (about 200-250 g of body weights), and randomly divided into two groups according to body weights, 5 rats in the sham operation group and 16 rats in the model group. All rats are anesthetized by intraperitoneal injection of 3% pentobarbital sodium (50 mg/kg); for the rats in the model group, the hair of the left and right knee joints is removed, disinfecting with 70% alcohol and iodine tincture and the left knee joint is bent 90 degrees to find the precise injection site, moving the needle of the syringe horizontally along the knee (so as not to pierce the skin) until a gap under the patella is found marking the area with slight pressure, then lifting the needle and syringe vertically, inserting the needle into the marked area, through the patellar tendon perpendicular to the tibia: and no resistance should be felt. Then MIA physiological saline solution (2 mg/50 µl) is injected into each articular cavity at both sides of the knee joints; and 50 µl of saline is injected into each articular cavity at the left and right sides of the knee joints in the sham operation group. After the injection, the knee is massaged to ensure an even distribution [38]. The preparation of MIA solution: MIA powder (Sigma, 57858-5G) is dissolved in physiological saline at a concentration of 40 mg/ml, and then filtering with a 0.22 µm filter membrane, and using right after it is ready. Three days after the MIA injection, the rats in the model group are subjected to a pain test. According to the test results, the rats are randomly divided into two groups: 8 rats in each group for the vehicle control group and the plasminogen group; then the administration starts, and the day of first administration is set as day 1. Each rat in the vehicle control group is injected with 0.7 ml of vehicle (10 mM sodium citrate buffer, 2% arginine hydrochloride, 3% mannitol, pH 7.4) in the tail vein every day, and the rats in the plasminogen group are administered with human plasminogen by tail vein injection at 7 mg/0.7 ml/rate/day. The administration is taken 7 consecutive days. Animal status is observed during the administration. On day 8, the pain tests are performed for the left and right legs 3.

Figure 9:
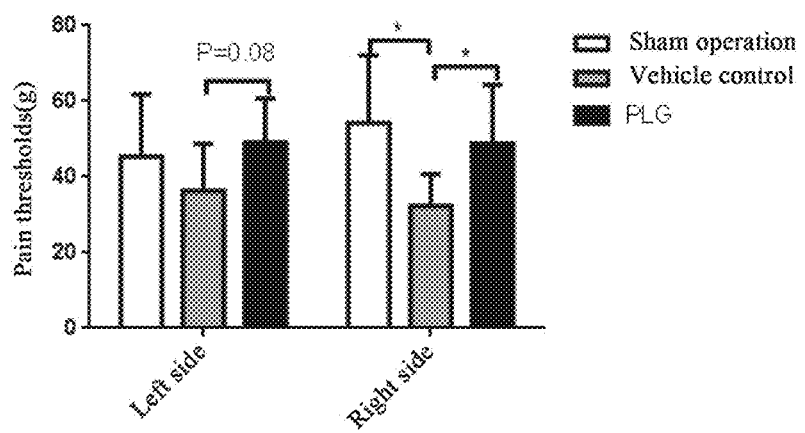
FIG. 9: Results of pain detection of MIA osteoarthritis model rats 7 days after the administration of plasminogen. The results show that the rats in the sham operation group have higher pain thresholds the pain thresholds of the left and right legs in the vehicle control group have significantly decreased, and are significantly lower than those in the sham operation group the pain thresholds of the left and right legs in the plasminogen group are significantly increased, compared with the vehicle control group, the statistical difference between the left legs is close to significance ($P=0.08$), and the statistical difference between the right legs is significant (* indicates $P<0.05$). The results show that plasminogen can significantly reduce the pain of osteoarthritis.

The results show that the rats in the sham operation group have relatively higher pain thresholds: the pain thresholds of the left and right legs in the vehicle control group are significantly lower, and are significantly lower than those in the sham operation group the pain thresholds of the left and right legs in the plasminogen group are significantly increased, compared with the vehicle control group, the statistical difference between the left legs is close to significance (P=0.08), and the statistical difference between the right legs is significant (* indicates P<0.05) (FIG. 9). The results show that plasminogen can significantly reduce the pain of osteoarthritis.

Example 10: Plasminogen Reduces Arthritis Pain in Osteoarthritis Model Mice

Nineteen 7-week-old C57 female mice are weighed and randomly divided into two groups according to body weights, 3 mice in the sham operation group and 16 mice in the model group. The mice in the model group are anesthetized by intraperitoneal injection of 3% pentobarbital sodium at 50 mg/kg body weight the hair on both sides of the back is removed, disinfecting with 70% alcohol and iodine tincture the skin, back muscles and peritoneum are cut open, and the white shiny fat tissue is gently pulled out through the incision by using small forceps so as to separate the fat tissue, and the ovaries can be seen. The fallopian tube at the lower end of ovary is ligated with silk thread, and then the ovary is removed. After anesthesia, for the mice in the sham operation group, only the skin, back muscles and peritoneum are cut open, and the ovaries are not removed. After suture and disinfection, all surgical mice are intramuscularly injected with antibiotics (5000U/mouse), and subcutaneously injected with analgesic (2 mg/kg). The injection is taken for 3 consecutive days. 65 days after the ovariectomy, all mice are intraperitoneally injected with pentobarbital sodium for anesthesia, removing the hair on the right knee, disinfecting with 70% alcohol and iodine tincture the right knee is bent 90 degrees to find the precise injection site, moving the needle of the syringe along the knee horizontally (so as not to pierce the skin) until a gap under the patella is found marking the area with slight pressure, then lifting the needle and syringe vertically, inserting the needle into the marked area, through the patellar tendon perpendicular to the tibia and no resistance should be felt. As for the model group mice, 5 µg/6 µl Type II collagenase physiological saline solution is injected into the right articular cavity of the mice: as for the sham operation group mice, 6 µl of physiological saline is injected into the right articular cavity of the mice [3].After the injection, the knee is massaged to ensure even distribution. The left knee joint is not treated with injection. 7 days after the collagenase injection, all mice are weighed. The mice in the model group are randomly divided into two groups according to their body weights, 8 mice in each of the vehicle control group and the plasminogen group; then the drugs are administered to the mice, and the day of first administration is set as day 1. The human plasminogen is administered to the plasminogen group mice by tail vein injection at 1 mg/0.1 ml/mouse/day, and the same volume of PBS buffer is injected into the tail vein of the vehicle control group mice for 28 consecutive days. The mice in the sham operation group are not t administered. The pain tests are performed for the right legs on day 29 [34].

Figure 10:
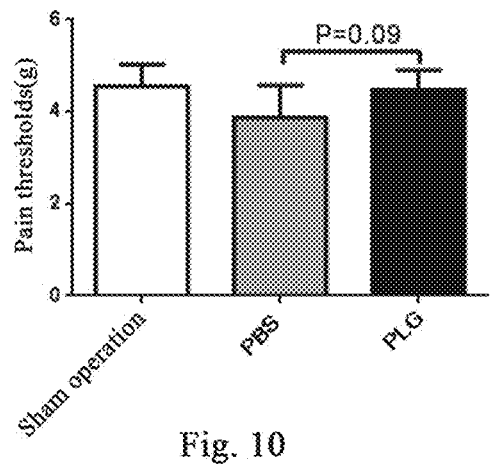
FIG. 10: Results of pain detection of osteoarthritis model mice 7 days after the administration of plasminogen. The results show that the pain thresholds of the mice in the sham operation group are relatively higher: the pain thresholds of the mice in the vehicle control group are significantly reduced, and are significantly lower than those in the sham operation group while the pain thresholds of the mice in the plasminogen group are significantly increased, and are significantly higher than those in the vehicle control group, and the statistical difference is close to significance ($P=0.09$). This result indicates that plasminogen can reduce osteoarthritis pain.

The results show that the pain thresholds of the mice in the sham operation group are relatively higher: the pain thresholds of the mice in the vehicle control group are significantly reduced, and are significantly lower than those in the sham operation group mice: while the pain thresholds of the mice in the plasminogen group are significantly increased, and are significantly higher than those in the vehicle control group mice, and the statistical difference is close to significance (P=0.09) (FIG. 10). This result indicates that plasminogen can reduce osteoarthritis pain.

Example 11: Plasminogen Promotes Cartilage Regeneration in Osteoarthritis Model Mice Nineteen 7-week-old C57 female mice are weighed and randomly divided into two groups according to body weights, 3 mice in the sham operation group and 16 mice in the model group. The mice in the model group are anesthetized by intraperitoneal injection of 3% pentobarbital sodium at 50 mg/kg body weight the hair on both sides of the back is removed, disinfecting with 70% alcohol and iodine tincture the skin, back muscles and peritoneum are cut open, and the white shiny fat tissue is gently pulled out from the incision by using small forceps so as to separate the fat tissue, and the ovaries can be seen. The fallopian tube at the lower end of ovary is ligated with silk thread, and then the ovary is removed. After anesthesia, for the mice in the sham operation group, only the skin, back muscles and peritoneum are cut open, and the ovaries are not removed. After suture and disinfection, all surgical mice are intramuscularly injected with antibiotics (5000U/mouse), and subcutaneously injected with analgesic (2 mg/kg). The injection is taken for 3 consecutive days. 65 days after the ovariectomy, all mice are intraperitoneally injected with pentobarbital sodium for anesthesia, removing the hair on the right knee, disinfecting with 70% alcohol and iodine tincture the right knee is bent 90 degrees to find the precise injection site, moving the needle of the syringe along the knee horizontally (so as not to pierce the skin) until a gap under the patella is found marking the area with slight pressure, then lifting the needle and syringe vertically, inserting the needle into the marked area, through the patellar tendon perpendicular to the tibia and no resistance should be felt. As for the model group mice, 5 μg/6 μl Type II collagenase physiological saline solution is injected into the right articular cavity of the mice; as for the sham operation group mice, 6 μl of physiological saline is injected into the right articular cavity of the mice [3]. After the injection, the knee is massaged to ensure even distribution. The left knee joint is not treated with injection. 7 days after the collagenase injection, all mice are weighed. The mice in the model group are randomly divided into two groups according to their body weights, 8 mice in each of the vehicle control group and the plasminogen group then the drugs are administered to the mice, and the day of first administration is set as day 1. The human plasminogen is administered to the plasminogen group mice by tail vein injection at 1 mg/0.1 ml/mouse/day, and the same volume of PBS buffer is injected into the tail vein of the vehicle control group mice for 28 consecutive days. The mice in the sham operation group are not administered. The mice are sacrificed on day 29, and the knee joints of both sides are taken and fixed in PLP fixative solution, then decalcifying in 10% EDTA for three weeks, washing with gradient sucrose solution, and embedding in paraffin, then slicing into 5 μm sections and staining with safranin O. The sections are observed and photographed under a 100× optical microscope, processing with Image-Pro software to collect data.

Figure 11:
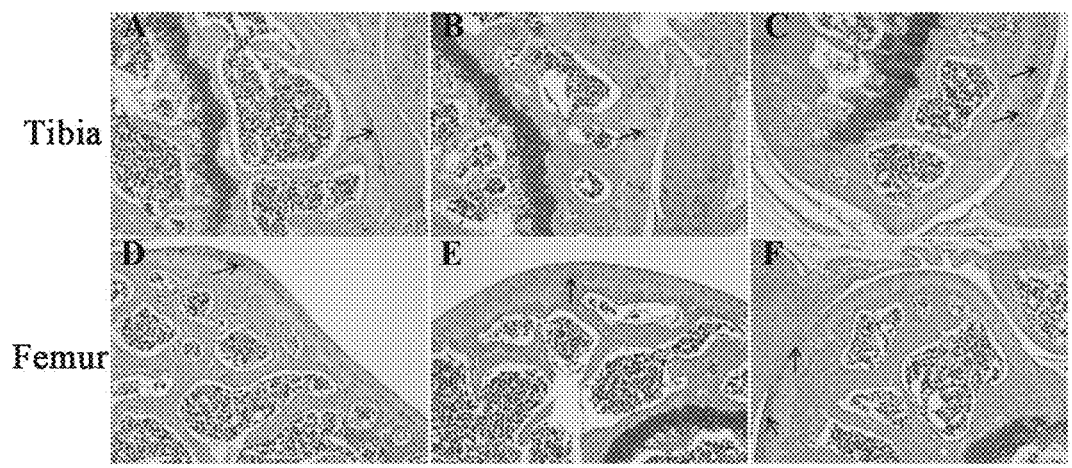
FIGS. 11A-11F: Results of Safranin O staining on the left knee joints of osteoarthritis model mice 28 days after the administration of plasminogen. The results show that there is a certain amount of articular cartilage (arrow marked) on the femur and tibia surfaces of the left knee joints in the sham operation group, there is no significant difference between the amount of cartilage on the tibia and femoral surfaces in the vehicle control group and that in the sham operation group, while the amount of cartilage in the plasminogen group is significantly higher than that in the vehicle control group and the sham operation group. It indicates that plasminogen can promote the regeneration of articular cartilage in osteoarthritis model mice.

The results show that there is a certain amount of articular cartilage (arrow marked) on the femur and tibia surfaces of the left knee joints in the sham operation group (FIGS. 11A, D), there is no significant difference between the amount of cartilage on the tibia and femur surfaces in the vehicle control group and that in the sham operation group, while the amount of cartilage in the plasminogen group (FIGS. 11C, F) is significantly higher than that in the vehicle control group and the sham operation group. It indicates that plasminogen can promote the regeneration of articular cartilage in osteoarthritis model mice.

Example 12: Plasminogen Inhibits Bone Resorption in Osteoarthritis Model Mice

Nineteen 7-week-old C57 female mice are weighed and randomly divided into two groups according to body weights, 3 mice in the sham operation group and 16 mice in the model group. The mice in the model group are anesthetized by intraperitoneal injection of 3% pentobarbital sodium at 50 mg/kg body weight the hair on both sides of the back is removed, disinfecting with 70% alcohol and iodine tincture the skin, back muscles and peritoneum are cut open, and the white shiny fat tissue is gently pulled out from the incision by using small forceps so as to separate the fat tissue, and the ovaries can be seen. The fallopian tube at the lower end of ovary is ligated with silk thread, and then the ovary is removed. After anesthesia, for the mice in the sham operation group, only the skin, back muscles and peritoneum are cut open, and the ovaries are not removed. After suture and disinfection, all surgical mice are intramuscularly injected with antibiotics (5000U/mouse), and subcutaneously injected with analgesic (2 mg/kg). The injection is taken for 3 consecutive days. 65 days after the ovariectomy, all mice are intraperitoneally injected with pentobarbital sodium for anesthesia, removing the hair on the right knee, disinfecting with 70% alcohol and iodine tincture the right knee is bent 90 degrees to find the precise injection site, moving the needle of the syringe along the knee horizontally (so as not to pierce the skin) until a gap under the patella is found marking the area with slight pressure, then lifting the needle and syringe vertically, inserting the needle into the marked area, through the patellar tendon perpendicular to the tibia and no resistance should be felt. As for the model group mice, 5 μg/6 μl Type II collagenase physiological saline solution is injected into the right articular cavity of the mice as for the sham operation group mice, 6 μl of physiological saline is injected into the right articular cavity of the mice [36,37]. After the injection, the knee is massaged to ensure even distribution. The left knee joint is not treated with injection. 7 days after the collagenase injection, all mice are weighed. The mice in the model group are randomly divided into two groups according to their body weights, 8 mice in each of the vehicle control group and the plasminogen group: then the administration starts, and the day of first administration is set as day 1. The human plasminogen is administered to the plasminogen group mice by tail vein injection at 1 mg/0.1 ml/mouse/day, and the same volume of PBS buffer is injected into the tail vein of the vehicle control group mice for 28 consecutive days. The mice in the sham operation group are not administered. The mice are sacrificed on day 29, and the knee joints of both sides are taken and fixed in PLP fixative solution, then decalcifying in 10% EDTA for three weeks, washing with gradient sucrose solution, sectioning into 5 μm, dewaxing and rehydrating, then staining with acid phosphatase (TRAP).

Figure 12:
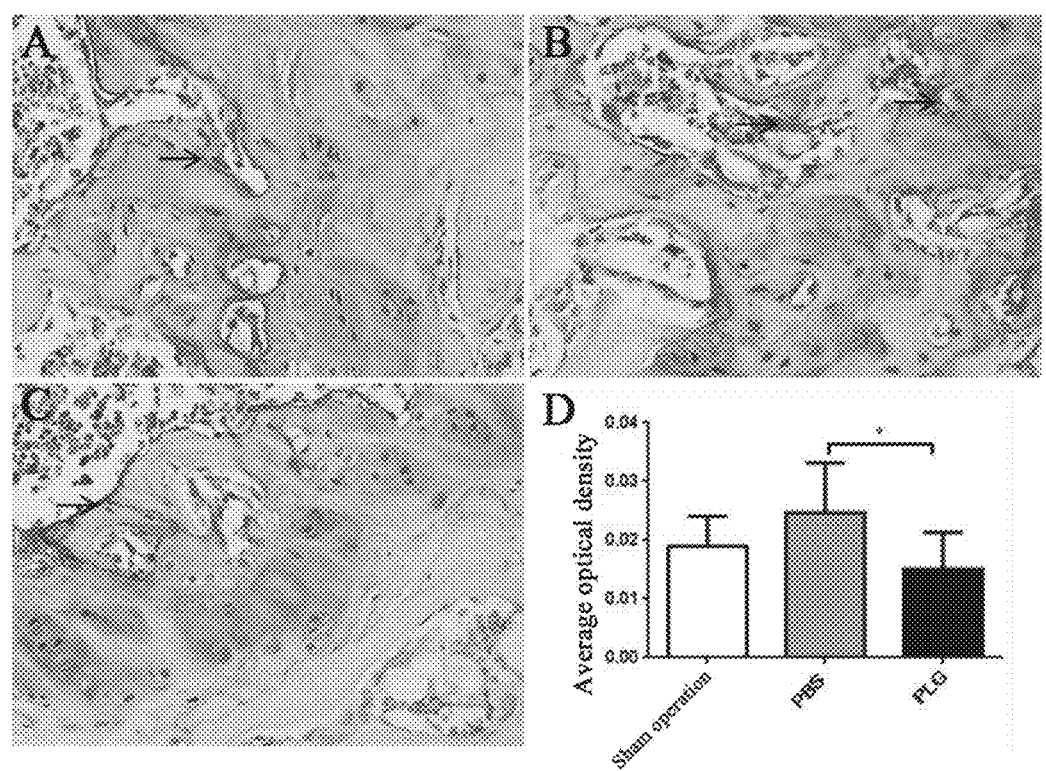
FIGS. 12A-12D show that plasminogen inhibits bone resorption in osteoarthritis model mice. The results show that there is a certain amount of acid phosphatase (arrow marked) in the knee joints of the sham operation group (FIG. 12A); the acid phosphatase of the knee joints in the vehicle control group is increased (FIG. 12B), and is significantly more than that of the sham operation group while the acid phosphatase of the knee joints in the plasminogen group (FIG. 12C) is significantly less than that in the vehicle control group, and the statistical difference is significant (* indicates $P<0.05$) (FIG. 12D). This result indicates that plasminogen can reduce acid phosphatase of osteoarthritis knee joint, reduce osteoclast activity, and inhibit bone resorption.

Acid phosphatase (TRAP) is a specific marker enzyme for osteoclasts, and osteoclasts are the main functional cells for bone resorption. The results show that there is a certain amount of acid phosphatase (arrow marked) in the knee joints of the sham operation group (FIG. 12A); the acid phosphatase of the knee joints in the vehicle control group is increased (FIG. 12B), and is significantly more than that of the sham operation group; while the acid phosphatase of the knee joints in the plasminogen group (FIG. 12C) is significantly less than that in the vehicle control group, and the statistical difference is significant (* indicates P<0.05) (FIG. 12D). This result indicates that plasminogen can reduce acid phosphatase of osteoarthritis knee joint, reduce osteoclast activity, and inhibit bone resorption.

Example 13: Plasminogen Promotes Increase of the Number of Sox 9 Positive Stem Cells in Tibial End of the Knee Joint in MIA Osteoarthritis Twenty five 8-10 weeks aged C57 male mice are weighed and randomly divided into two groups according to body weights 5 mice in the sham operation group, and 20 mice in the model group. All mice are anesthetized by intraperitoneal injection of 3% pentobarbital sodium at 50 mg/kg body weight. After anesthesia, for the mice in the model group, the hair of the left knee is removed, disinfecting with 70% alcohol and iodine tincture: and the left knee joint is bent 90 degrees, moving the needle of the syringe horizontally along the knee (so as not to pierce the skin) until a gap under the patella is found marking the area with slight pressure, then lifting the needle and syringe vertically, inserting the needle into the marked area, through the patellar tendon perpendicular to the tibia, and MIA physiological saline solution is injected into the articular cavity at 0.1 mg/10 μl; in the sham operation group, 10 μl saline is injected into the left articular cavity, after the injection, massaging the knee to ensure even distribution [34]. The right knee joint is not treated. Three days after the MIA injection in the articular cavity, the mice in the model group are subjected to a pain test. According to the test results, the mice are randomly divided into two groups: 10 mice in each group for the vehicle control group and the plasminogen group then the drugs are administered to the mice, and the day of first administration is set as day 1. The human plasminogen is administered to the plasminogen group mice by tail vein injection at 1 mg/0.1 ml/mouse/day, and the same volume of PBS buffer is injected into the tail vein of the vehicle (PBS) control group mice for 28 consecutive days. The mice in the sham operation group are not treated with administration. The preparation of MIA solution: MIA powder (Sigma, 57858-5G) is dissolved in physiological saline at a concentration of 10 mg/ml, and then filtering with a 0.22 μm filter membrane, and using right after it is ready. The mice are sacrificed on day 29, and the left knee joints are taken and fixed in PLP fixative solution, then decalcifying in 10% EDTA for three weeks, washing with gradient sucrose solution, and embedding in paraffin. The thickness of the tissue section is 5 μm, and the sections are washed once after dewaxing and rehydrating. The tissues are circled with a PAP pen, then incubating with 3% hydrogen peroxide for 15 min, and washing twice with 0.01M PBS for 5 min each time. 5% normal sheep serum (Vector laboratories, Inc., USA) is used to block for 30 min after the time is expired, the sheep serum is discarded, then adding rabbit-derived anti-Sox 9 antibody (Abcam, ab185966) dropwise, incubating overnight at 4° C., and washing twice with 0.01M PBS for 5 min each time. Goat anti-rabbit IgG (HRP) antibody (Abcam) (secondary antibody) is incubated for 1 hour at room temperature, then washing twice with 0.01M PBS for 5 min each time. Color development is performed according to the DAB kit (Vector laboratories, Inc., USA), after washing three times with water, counterstaining with hematoxylin for 30 seconds, and rinsing under running water for 5 min. Dehydration is performed with gradient alcohol, then making transparent with xylene and sealing with neutral gum; and the sections are observed and photographed under 100× (A-C) and 400× (D-F) optical microscopes, processing with Image-Pro software to collect data.

Sox9 is a key transcription factor in the process of cartilage development and formation, and it determines the mesenchymal stem cells aggregation and differentiation into chondrocytes, playing an important role in regulating the process of cartilage development, maturation and repair [39].

Figure 13:
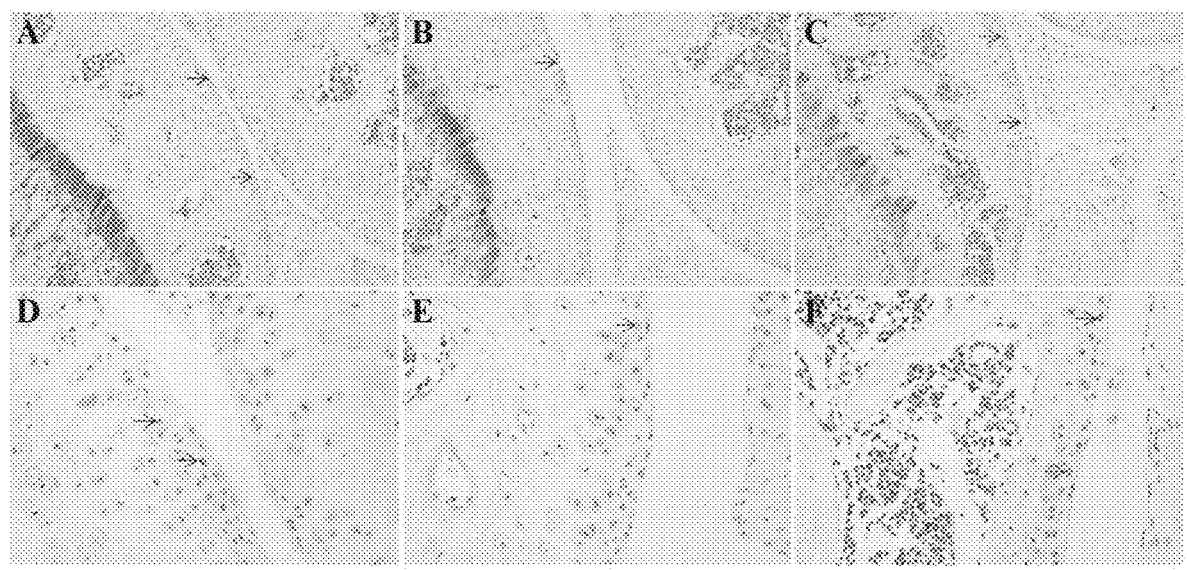
FIGS. 13A-13F show that plasminogen promotes an increase in the number of Sox-9 positive stem cells at the tibial end of the knee joint of MIA osteoarthritis. The results show that there is a certain amount of Sox 9 positive stem cells (arrow marked) in the knee joint tibia in the sham operation group (FIG. 13A, FIG. 13D); the number of Sox 9 positive stem cells in the knee joint tibia in the vehicle control group (FIG. 13B, FIG. 13E) is significantly reduced, while in the plasminogen group (FIG. 13C, FIG. 13F) the number of Sox 9 positive stem cells in the knee joint tibia is significantly higher than that in the vehicle control group. This result indicates that plasminogen can promote the increase of the number of Sox-9 positive stem cells in the tibial end of osteoarthritis knee joint, and repair the knee joint injury caused by osteoarthritis.

The results show that there is a certain amount of Sox 9 positive stem cells (arrow marked) in the knee joint tibia in the sham operation group (FIGS. 13A, D); the number of Sox 9 positive stem cells in the knee joint tibia in the vehicle control group (FIGS. 13B, E) is significantly reduced, while in the plasminogen group (FIGS. 13C, F) the number of Sox 9 positive stem cells in the knee joint tibia is significantly higher than that in the vehicle control group. This result indicates that plasminogen can promote increase of the number of Sox-9 positive stem cells in the tibial end of osteoarthritis knee joint, and repair the knee joint injury caused by osteoarthritis.

Example 14: Plasminogen Improves Inflammation Condition of Knee Joint Synovium in MIA Osteoarthritis Model Mice Twenty five 8-10 weeks aged C57 male mice are weighed and randomly divided into two groups according to body weights 5 mice in the sham operation group, and 20 mice in the model group. All mice are anesthetized by intraperitoneal injection of 3% pentobarbital sodium at 50 mg/kg body weight. After anesthesia, for the mice in the model group, the hair of the left knee is removed, disinfecting with 70% alcohol and iodine tincture: and the left knee joint is bent 90 degrees, moving the needle of the syringe horizontally along the knee (so as not to pierce the skin) until a gap under the patella is found marking the area with slight pressure, then lifting the needle and syringe vertically, inserting the needle into the marked area, through the patellar tendon perpendicular to the tibia, and MIA physiological saline solution is injected into the articular cavity at 0.1 mg/10 μl; in the sham operation group, 10 μl saline is injected into the left articular cavity, after the injection, massaging the knee to ensure even distribution [34]. The right knee joint is not treated. Three days after the MIA injection in the articular cavity, the mice in the model group are subjected to a pain test. According to the test results, the mice are randomly divided into two groups: 10 mice in each group for the vehicle control group and the plasminogen group then the drugs are administered to the mice, and the day of first administration is set as day 1. The human plasminogen is administered to the plasminogen group mice by tail vein injection at 1 mg/0.1 ml/mouse/day, and the same volume of PBS buffer is injected into the tail vein of the vehicle (PBS) control group mice for 28 consecutive days. The mice in the sham operation group are not administered. The preparation of MIA solution: MIA powder (Sigma, 57858-5G) is dissolved in physiological saline at a concentration of 10 mg/ml, and then filtering with a 0.22 μm filter membrane, and using right after it is ready. The mice are sacrificed on day 29, and the left knee joints are taken and fixed in PLP fixative solution, then decalcifying in 10% EDTA for three weeks, washing with gradient sucrose solution, and embedding in paraffin (preserving muscles around the knee joint). The thickness of the tissue section is 5 μm, and the sections are dewaxed and rehydrated, then staining with hematoxylin and eosin (H & E staining), differentiating with 1% hydrochloric acid-alcohol solution, blueing with aqueous ammonia, and then dehydrating with alcohol gradient, making transparent with xylene, sealing with neutral gum; and the sections are observed under 400× optical microscope.

Figure 14:
FIGS. 14A-14C show that plasminogen improves knee joint synovial inflammation in MIA osteoarthritis model mice. The results show that there is no obvious inflammatory cell infiltration in the knee joint synovium in the sham operation group (FIG. 14A); while in the vehicle control group (FIG. 14B), there is obvious inflammation cell infiltration (arrow marked) in the knee joint synovium, and in the plasminogen group (FIG. 14C) the infiltration of inflammatory cells in the synovium of the knee joints is significantly less than that in the vehicle control group. This result indicates that plasminogen can improve inflammation condition of the knee joint synovium in osteoarthritis.

The results show that there is no obvious inflammatory cell infiltration in the knee joint synovium in the sham operation group (FIG. 14A); while in the vehicle control group (FIG. 14B), there is obvious inflammation cell infiltration (arrow marked) in the knee joint synovium, and in the plasminogen group (FIG. 14C) the infiltration of inflammatory cells in the synovium of the knee joints is significantly less than that in the vehicle control group. This result indicates that plasminogen can improve inflammation condition of the knee joint synovium in osteoarthritis.

The (human) plasminogen used in all of the above examples is derived from human donor plasma, and it is purified from human plasma based on the method described in the document [40-42] with process optimization. The purity of plasminogen monomer is higher than 95%.

REFERENCES

[1] National Institute of Arthritis and Musculoskeletal and Skin Diseases. April 2015. Archived from the original on 18 May 2015. Retrieved 13 May 2015.
[2] Glyn-Jones S. Palmer A J, Agricola R. Price A J, Vincent T L, Weinans H. Carr A J (July 2015). "Osteoarthritis". Lancet. 386 (9991): 376-87.
[3] Berenbaum F (January 2013). "Osteoarthritis as an inflammatory disease (osteoarthritis is not osteoarthrosis!)". Osteoarthritis and Cartilage. 21 (1): 16-21.

[4] Li G Yin J. Gao J Cheng T S, Pavlos N J, Zhang C. Zheng M H (2013). "Subchondral bone in osteoarthritis: insight into risk factors and microstructural changes".
[5] Alexander C M and Werb, Z. (1991). Extracellular matrix degradation. In Cell Biology of Extracellular Matrix, Hay E D, ed. (New York: Plenum Press), pp. 255-302.
[6] Werb, Z., Mainardi, C. L., Vater, C. A., and Harris, E. D., Jr. (1977). Endogenous activation of latent collagenase by rheumatoid synovial cells. Evidence for a role of plasminogen activator. N. Engl. J. Med. 296, 1017-1023.
[7] He, C. S., Wilhelm, S. M., Pentland, A. P., Marmer, B. L. Grant, G A., Eisen, A. Z., and Goldberg, G I. (1989). Tissue cooperation in a proteolytic cascade activating human interstitial collagenase. Proc. Natl. Acad. Sci. U.S.A 86, 2632-2636.
[8] Stoppelli, M. P., Corti, A., Soffientini, A., Cassani, G., Blasi, F., and Assoian, R. K. (1985). Differentiation-enhanced binding of the amino-terminal fragment of human urokinase plasminogen activator n a specific receptor on U937 monocytes. Proc. Natl. Acad. Sci. U.S.A 82, 4939-4943.
[9] Vassalli, J. D., Baccino, D., and Belin, D. (1985). A cellular binding site for the Mr 55,000 form of the human plasminogen activator, urokinase. J. Cell Biol. 100, 86-92.
[10] Wiman, B. and Wallen, P. (1975). Structural relationship between "glutamic acid" and "lysine" forms of human plasminogen and their interaction with the NH2-terminal activation peptide as studied by affinity chromatography. Eur. J. Biochem. 50, 489-494.
[11] Saksela, O. and Rifkin, D. B. (1988). Cell-associated plasminogen activation: regulation and physiological functions. Annu. Rev. Cell Biol. 4, 93-126.
[12] Raum, D., Marcus, D., Alper, C. A., Levey, R., Taylor, P. D., and Starzl, T. E. (1980). Synthesis of human plasminogen by the liver. Science 208, 1036-1037.
[13] David M. Waisman. Plasminogen: structure, activation, and regulation. Springer US, 2003.
[14] Sottrup-Jensen, L., Zajdel, M., Claeys, H., Petersen, T. E., and Magnusson, S. (1975). Amino-acid sequence of activation cleavage site in plasminogen: homology with "pro" part of prothrombin. Proc. Natl. Acad. Sci. U.S.A 72, 2577-2581.
[15] Collen, D. and Lijnen, H. R. (1991). Basic and clinical aspects of fibrinolysis and thrombolysis. Blood 78, 3114-3124.
[16] Alexander, C. M. and Werb, Z. (1989). Proteinases and extracellular matrix remodeling. Curr. Opin. Cell Biol. 1, 974-982.
[17] Mignatti, P. and Rifkin, D. B. (1993). Biology and biochemistry of proteinases in tumor invasion. Physiol Rev. 73, 161-195.
[18] Collen, D. (2001). Ham-Wasserman lecture: role of the plasminogen system in fibrin-homeostasis and tissue remodeling. Hematology. (Am. Soc. Hematol. Educ. Program.) 1-9.
[19] Rifkin, D. B., Moscatelli, D., Bizik, J., Quarto, N., Blei, F. Dennis, P., Flaumenhaft, R., and Mignatti, P. (1990). Growth factor control of extracellular proteolysis. Cell Differ. Dev. 32, 313-318.
[20] Andreasen, P. A., Kjoller, L., Christensen, L., and Duffy, M J. (1997). The urokinase-type plasminogen activator system in cancer metastasis: a review. Int. J. Cancer 72, 1-22.
[21] Rifkin, D. B., Mazzieri, R., Munger, J. S., Noguera, I., and Sung, J. (1999). Proteolytic control of growth factor availability. APMIS 107, 80-85.
[22] Marder V J Novokhatny V. Direct fibrinolytic agents: biochemical attributes, preclinical foundation and clinical potential [J]. Journal of Thrombosis and Haemostasis, 2010, 8(3): 433-444.
[23] Hunt J A. Petteway Jr S R. Scuderi P. et al. Simplified recombinant plasmin: production and functional comparison of a novel thrombolytic molecule with plasma-derived plasmin [J]. Thromb Haemost, 2008, 100(3):413-419.
[24] Medynski D, Tuan M, Liu W, et al. Refolding, purification, and activation of miniplasminogen and microplasminogen isolated from E. coli inclusion bodies.[J]. Protein Expression & Purification, 2007, 52(2):395-402.
[25] Nagai N. Demarsin E, Van Hoef B. et al. Recombinant human microplasmin: production and potential therapeutic properties [J]. Journal of Thrombosis and Haemostasis, 2003, 1(2): 307-313.
[26] E. DACI, A. VERSTUYF, K. MOERMANS et al. Bone Resorption Induced by 1a,25 Dihydroxyvitamin D3 In Vivo Is Not Altered by Inactivation of the Plasminogen Activator Inhibitor 1. Bone Vol. 27, No. 1 Jul. 2000:97-102.
[27] Mohammed S. Razzaque, Despina Sitara, Takashi Taguchi et al. Premature aging-like phenotype in fibroblast growth factor 23 null mice is a vitamin D-mediated process. FASEB J. 2006 April; 20(6): 720-722.
[28] Mackay, A. M., Beck, S. C., Murphy, J. M., Barry, F. P., Chichester, C. O., & Pittenger, M. F. (1998). Chondrogenic differentiation of cultured human mesenchymal stem cells from marrow. Tissue Engineer. 4:415-428.
[29] Peter L. E. M. van Lent, Arjen B. Blom, Rik F. P. Schelbergen et al. Active Involvement of Alarmins S100A8 and S100A9 in the Regulation of Synovial Activation and Joint Destruction During Mouse and Human Osteoarthritis. Arthritis Rheum. 2012 May 64(5): 1466-76. doi: 10.1002/art.34315.
[30] Peter M. van der Kraan, Elly L. Vitters, Henk M. van Beuningen et al. Degenerative knee joint lesions in mice after a single intra-articular collagenase injection. A new model of osteoarthritis. J Exp Pathol (Oxford). 1990 February; 71(1):19-31.
[31] Ostergaard K, Andersen C B, Petersen J et al. Validity of histopathological grading of articular cartilage from osteoarthritic knee joints. Ann Rheum Dis. 1999 April; 58(4): 208-13.
[32] Weinreb M. Shinar D. Rodan G Different pattern of alkaline phosphatase, osteopontin, and osteocalcin expression in developing rat bone visualized by in situ hybridization J. J Bone Miner Res, 1990, 5 (8): 831-842.
[33] S. Kamekura M. D.y, K. Hoshi M. D., Ph.D et al. Osteoarthritis development in novel experimental mouse models induced by knee joint instability. Osteoarthritis Cartilage. 2005 July:13(7): 632-41.
[34] Ogbonna A C, Clark A K et al. Pain-like behavior and spinal changes in the monosodium iodoacetate model of osteoarthritis in C57Bl/6 mice. Eur J Pain. 2013 April; 17(4): 514-26.
[35] Keigo Sato, Hisashi Mera, Shigeyuki Wakitani et al. Effect of epigallocatechin-3-gallate on the increase in type II collagen accumulation in cartilage-like MSC sheets. Journal of the Agricultural Chemical Society of Japan, 2017, 81(6):5.
[36] Gustavo Duque, Dao Chao Huang, Natalie Dion et al. Interferon-g Plays a Role in Bone Formation In Vivo and Rescues Osteoporosis in Ovariectomized Mice. Journal of Bone and Mineral Research. Vol. 26, No. 7, July 2011, pp 1472-1483.

[37] Peter M. van der Kraan, Elly L. Vitters, Henk M. van Beuningen, et al. Degenerative knee joint lesions in mice after a single intra-articular collagenase injection. A new model of osteoarthritis. J Exp Pathol (Oxford). 1990 February; 71(1): 19-31.

[38] Combe R. Bramwell S. Field M J et al. The monosodium iodoacetate model of osteoarthritis: a model of chronic nociceptive pain in rats? Neurosci Lett. 2004 Nov. 11; 370(2-3): 236-40.

[39] Hardingham T E, Oklershaw R A. Tew S R. Cartilage, SOX9 and Notch signals in chondrogenesis [J]. Journal of Anatomy, 2010, 209(4): 469-480.

[40] Kenneth C Robbins, Louis Summaria, David Elwyn et al. Further Studies on the Purification and Characterization of Human Plasminogen and Plasmin. Journal of Biological Chemistry, 1965, 240 (1): 541-550.

[41] Summaria L. Spitz F. Arzadon L et al. Isolation and characterization of the affinity chromatography forms of human Glu- and Lys-plasminogens and plasmins. J Biol Chem. 1976 Jun. 25; 251(12): 3693-9.

[42] HAGAN J J ABLONDI F B, DE RENZO E C. Purification and biochemical properties of human plasminogen. J Biol Chem. 1960 April; 235: 1005-10.

The invention claimed is:

1. A method for treating osteoarthritis, which includes administering an effective amount of plasminogen to a subject.

2. The method according to claim 1, the plasminogen increases the amount of articular cartilage, and/or promotes the repair of articular cartilage injury.

3. The method according to claim 1, the plasminogen improves the inflammation condition of joint synovium.

4. The method according to claim 1, the plasminogen promotes the bone remodeling of subchondral bone for joints.

5. The method according to claim 1, wherein the plasminogen improves the inflammation condition and pain of joint, and/or improves joint function.

6. The method according to claim 1, wherein the plasminogen reduces joint swelling and pain.

7. The method according to claim 1, wherein the plasminogen has at least 75%, 80%, 85%, 90%, 95%, 96%, 97%, 98%, or 99% sequence identity with SEQ ID NO: 2, and has plasminogen activity.

8. The method according to claim 1, wherein the plasminogen is a protein comprising a plasminogen active fragment and having plasminogen activity.

9. A method for promoting the regeneration of articular cartilage in an osteoarthritis subject, which includes administering an effective amount of plasminogen to the subject.

10. The method according to claim 9, wherein the plasminogen has at least 80%, 85%, 90%, 95%, 96%, 97%, 98%, or 99% sequence identity with SEQ ID NO: 2, and has plasminogen activity.

11. A method for promoting the repair of joint injury in a subject, which includes administering an effective amount of plasminogen to the subject.

12. The method according to claim 11, wherein the plasminogen promotes the regeneration of articular cartilage and/or the bone remodeling of subchondral bone.

13. The method according to claim 11, wherein the subject is an osteoarthritis subject.

14. The method according to claim 11, wherein the plasminogen improves the inflammation condition of joint tissue, and/or reduces joint pain.

15. The method according to claim 11, wherein the plasminogen has at least 80%, 85%, 90%, 95%, 96%, 97%, 98%, or 99% sequence identity with SEQ ID NO: 2, and has plasminogen activity.

\* \* \* \* \*